(12) United States Patent
Belinsky et al.

(10) Patent No.: US 7,214,485 B2
(45) Date of Patent: May 8, 2007

(54) NESTED METHYLATION-SPECIFIC POLYMERASE CHAIN REACTION CANCER DETECTION METHOD

(75) Inventors: Steven A. Belinsky, Albuquerque, NM (US); William A. Palmisano, Edgewood, NM (US)

(73) Assignee: Lovelace Respiratory Research Institute, Albuquerque, NM (US)

( * ) Notice: Subject to any disclaimer, the term of this patent is extended or adjusted under 35 U.S.C. 154(b) by 577 days.

(21) Appl. No.: 10/344,815

(22) PCT Filed: Aug. 24, 2001

(86) PCT No.: PCT/US01/26452

§ 371 (c)(1),
(2), (4) Date: Feb. 14, 2003

(87) PCT Pub. No.: WO02/18649

PCT Pub. Date: Mar. 7, 2002

(65) Prior Publication Data

US 2004/0038245 A1 Feb. 26, 2004

Related U.S. Application Data

(60) Provisional application No. 60/228,057, filed on Aug. 25, 2000.

(51) Int. Cl.
C12Q 1/68 (2006.01)
C12P 19/34 (2006.01)
C07H 21/04 (2006.01)

(52) U.S. Cl. .......................... 435/6; 435/91.2; 435/91.1; 536/24.3

(58) Field of Classification Search .................... 435/6, 435/91.2, 91.1; 536/24.3
See application file for complete search history.

(56) References Cited

U.S. PATENT DOCUMENTS

| | | | |
|---|---|---|---|
| 4,683,202 A | 7/1987 | Mullis | |
| 5,556,773 A | 9/1996 | Yourno | |
| 5,565,331 A | 10/1996 | Tessier-Lavigne et al. | |
| 5,693,467 A | 12/1997 | Roblin, III et al. | |
| 5,786,146 A | 7/1998 | Herman et al. | |
| 5,843,649 A | 12/1998 | Stoerker et al. | |
| 5,871,917 A | 2/1999 | Duffy | |
| 5,948,624 A | 9/1999 | Rothschild et al. | |
| 5,965,722 A | 10/1999 | Ecker et al. | |
| 6,017,704 A | 1/2000 | Herman et al. | |
| 6,033,858 A | 3/2000 | Bastian | |
| 6,117,635 A | 9/2000 | Nazarenko et al. | |
| 6,143,504 A | 11/2000 | Das et al. | |
| 6,200,756 B1 * | 3/2001 | Herman et al. ................ | 435/6 |
| 6,251,594 B1 * | 6/2001 | Gonzalgo et al. .............. | 435/6 |
| 6,255,293 B1 * | 7/2001 | Kimchi ........................ | 514/49 |
| 6,331,393 B1 * | 12/2001 | Laird et al. .................... | 435/6 |
| 6,709,818 B1 * | 3/2004 | Nelson et al. ................ | 435/6 |
| 6,818,404 B2 * | 11/2004 | Shuber ........................ | 435/6 |

FOREIGN PATENT DOCUMENTS

| | | |
|---|---|---|
| EP | 0 519 338 A1 | 6/1991 |
| JP | 406090756 A | 4/1994 |
| WO | WO99/63110 A1 | 12/1999 |
| WO | WO 01/06005 A2 | 1/2001 |

OTHER PUBLICATIONS

Sato et al. Hum. Genet. 1998, vol. 103, p. 96-101.*
Hendricks et al. Cancer Research, 1997, vol. 57, p. 2112-2115.*
Virmani et al. Journal of the National Cancer Institute, Aug. 16, 2000, vol. 92(16), p. 1303-1307.*
Ahrendt, S.A., et al., "Mollecular Detection of Tumor Cells in Bronchoalveolar Lavage Fluid from Patients with Early Stage Lung Cancer," *J Natl. Cancer Inst.*, vol. 91, No. 4, pp. 332-339 (Feb. 17, 1999).
Belinsky, S.A., et al., "aberrant Methylation of $p16^{OML4a}$ is an Early Event in Lung Cancer and a Potential Biomarker for Early Diagnosis," *Proc. Natl. Acad. Sci. USA*, vol. 95, pp. 11891-11896 (Sep. 1998).
Danbara, M., et al., "DNA Methylation Dominates Transcriptional Silencing of Pax5 in Terminally Differentiated B Cell Lines," *Molecular Immunology*, vol. 38, pp. 1161-1166 (2001).
Esteller, M., et al., "Detection of Aberrant Promotor Hypermethylation of Tumor Suppressor Genes in Serus DNA from Non-Small Cell Lung Cancer Patients," *Cancer Research*, vol. 59, pp. 67-70 (Jan. 1, 1999).
Esteller, M., et al., "Inactivation of the DNA Repair Gene $O^6$-Methylguanine-DNA Methyltransferase by Promoter Hypermethylation is a Common Event in Primary Human Neoplasia," *Cancer Research*, vol. 59, pp. 793-797 (Feb. 15, 1999).
Fliss, M.S., et al., "Facile Detection of Mitochondrial DNA Mutations in Tumors and Bodily Fluids," *Science*, vol. 287, pp. 2017-2019, (Mar. 17, 2000).

(Continued)

*Primary Examiner*—Kenneth R. Horlick
*Assistant Examiner*—Joyce Tung
(74) *Attorney, Agent, or Firm*—Janeen Vilven; Peacock Myers, P.C.

(57) ABSTRACT

A molecular marker-based method for monitoring and detecting cancer in humans. Aberrant methylation of gene promoters is a marker for cancer risk in humans. A two-stage, or "nested" polymerase chain reaction method is disclosed for detecting methylated DNA sequences at sufficiently high levels of sensitivity to permit cancer screening in biological fluid samples, such as sputum, obtained non-invasively. The method is for detecting the aberrant methylation of the p16 gene, O 6-methylguanine-DNA methyltransferase gene, Death-associated protein kinase gene, RAS-associated family 1 gene, or other gene promoters. The method offers a potentially powerful approach to population-based screening for the detection of lung and other cancers.

35 Claims, 12 Drawing Sheets

OTHER PUBLICATIONS

Gazdar, A.F., et al., "Molecular Detection of Early Lung Cancer," *J Natl Cancer Inst.*, vol. 91, No. 4, pp. 299-301 (Feb. 17, 1999).

Gonzalgo, M.L., et al., "Identification and Characterizationof Differentially Methylated Rgions of Genomic DNA by Methylation-Sensitive Arbitrarily Primed PCR," *Cancer Research*, vol. 57, pp. 594-599 (Feb. 15, 1997).

Greenblatt, M.S., "Mutations in the *p53* Tumor Supressor Gene: Clues to Cancer Etiology and Molecular Pathogenesis," *Cancer Research*, vol. 54, pp. 4855-4878 (Sep. 15, 1994).

Hara, E., et al., "Regulation of p16*CDKN2* Expression and its Implications for Cell Immortalization and Senescence," *Molecular and Cellular Biology*, pp. 859-867 (Mar. 1996).

Herman, J.G., et al., "Methylation-Specific PCR: A Novel PCT Assay for Methylation Status of CpG Islands," *Proc. Natl. Acad. Sci. USA*, vol. 93, pp. 9821-9826 (Sep. 1996).

Huang, T.H-M, et al., "Identification of DNA Methylation Markers for Human Breast Carcinomas Using the Methylation-Sensitive Restriction Fingerprinting Technique," *Cancer Research*, vol. 57, pp. 1030-1034 (Mar. 15, 1997).

Issa, J-P J., et al., "*H1C1* Hypermethylation is a Late Event in Hemotopoietic Neoplasms," *Cancer Research*, vol. 57, pp. 1678-1681 (May 1, 1997).

Johnson, D.H., et al., "Recent Advances with Chemotherapy for NSCLC: The ECOG Experience," *Oncology, Suppl No. 2*, pp. 67-69 (Jan. 1998).

Kaneko, M., et al., "Peripheral Lung Cancer: Screening and Detection with Low-Dose Spiral CT Versus Radiography, *Radiology*, vol. 201, pp. 798-802 (Dec. 1996).

Kashiwabara, K., et al., "Correlation Between Methylation Status of the *p16/CDKN2* Gene and the Expression of p16 and Rb Proteins in Primary Non-Small Cell Lung Cancers," *Int. J. Cancer (Pred. Oncol.)*, vol. 79, pp. 215-220 (Nov. 1997).

Kratzke, R.A., et al., "*Rb* and p16$^{INK4a}$ Expression in Resected Non-Small Cell Lung Tumors," *Cancer Research*, vol. 56, pp. 3415-3420 (Aug. 1, 1996).

Landis, S.H., et al., "Cancer Statistics, 1998," *CA-A Cancer J for Clinicians*, vol. 18, No. 1, pp. 6-29 w/ erratum (Jan./Feb. 1998).

Law, M.R., et al., "The Dose-Response Relationship Between Cigarette Consumption, Biochemical Markers and Risk of Lung Cancer," *British J of Cancer*, vol. 75, No. 11, pp. 1690-1693 (1997).

Lubin, J.H., et al., "Lung Cancer in Radon-Exposed Miners and Estimation of Risk from Indoor Exposure," *J Natl Cancer Inst.*, vol. 87, No. 11, pp. 817-827 (Jun. 7, 1995).

Mao, L, et al., "Detection of Oncogene Mutations in Sputum Precedes Diagnosis of Lung Cancer," *Cancer Research*, vol. 54, pp. 1634-1637 (Apr. 1, 1994).

Mao, L., et al., "Microsatellite Alterations as Clonal Markers for the Detection of Human Cancer," *Proc. Natl. Acad. Sci. USA*, vol. 91, pp. 9871-9875 (Oct. 1994).

Palmisano, W.A., et al., "Predicting Lung Cancer by Detecting Aberrant Promoter Methylation in Sputum," *Cancer Research*, vol. 60, pp. 5954-5958 (Nov. 1, 2000).

Rodenhuis, S., "*RAS* Oncogenes and Human Lung Cancer," *Lung Cancer: Principles and Practice*, edited by Harvy L. Pass, et al., Lippincott-Raven Publ, Phila PA pp. 73-82 (1996).

Saccomanno, G., et al., "Development of Carcinoma of the Lung as Reflected in Exfoliated Cells," *Cancer*, vol. 33, pp. 256-270 (1974).

Serrano, M., et al., "Role of the *INK4a* Locus in Tumor Suspension and Cell Mortality," *Cell*, vol. 85, pp. 27-37, (Apr. 5, 1996).

Sone, S., et al., "Mass Screening for Lung Cancer with Mobile Spiral Computed Tomography Scanner," *The Lancet*, vol. 351, pp. 1242-1245 (Apr. 25, 1998).

Swafford, D.S., et al., "Frequent Aberrant Methylation of *p16INK4A* IN Primary Rat Lung Tumors," *Mollecular and Cellular Biology*, pp. 1366-1374 (Mar. 1997).

Toyota, M., et al., "Identification of Differentially Methylated Sequencesin Colorectal Cancer by Methylated CpG Island Amplification," *Cancer Research*, vol. 59, pp. 2307-2312 (May 15, 1999).

Toyota, M., et al., "CpG Island Methylator Phenotype in Colorectal Cancer," *Proc. Natl Acad Sci USA*, vol. 96, pp. 8681-8686 (Jul. 1999).

Toyota, M., et al., Inactivation of *CACNA1G*, a T-Type Calcium Channel Gene, by Aberrant Methylation of Its 5' CpG Island in Human Tumors, *Cancer Research*, vol. 59, pp. 4535-4541 (Sep. 15, 1999).

Zheng, S., et al., "Correlations of Partial and Extensive Methylation at the p14$^{ARF}$ Locus with Reduced mRNA Expression in Colorectal Cancer Cell Lines and Clinicopathological Features in Primary Tumors," *Carcinogenesis*, vol. 21, No. 11, pp. 2057-2064 (2000).

Albert, Jan , et al., "Simple, Sensitive, and Specific Detection of Human Immunodeficiency Virus Type 1 Clinical Specimens by Polyermase Chain Reaction with Nested Primers", *Journal of Clinical Microbiology*, (Jul. 1990), 1560-1564.

Dammann, Reinhard , et al., "Epigenetic Inactivation of a RAS Association Domain Family Protein from the Lung Tumour Supressor Locus 2p21.3", *Nature Genetics*, vol. 25, (Jul. 2000).

Esteller, Manel , et al., "Detection of Aberrant Promoter Hypermethylation of Tumor Suppressor Genes in Serum DNA from Non-Small Cell Lung Cancer Patients", *Cancer Research* vol. 59,, (Jan. 1, 1999),pp. 67-70.

Herman, James G., et al., "Methylation-Specific PCR: A Novel PCR Assay for Methylation Status of CpG Islands", *Proc. Natl. Acad Sci. USA.* vol. 93, (Sep. 1996),9821-9826.

Sato, Masami , et al., "The H-Cadherin (CDH13) Gene is Inactivated in Human Lung Cancer", *Hum Genet.* vol. 103, (Jul. 1998),96-101.

Tanaka, Hisashi , et al., "Methylation of the 5' CpG Island of the FHIT Gene is Closely Associated with Transcriptional Inactivation in Esophageal Squamous Cell Carcinomas", *Cancer Research*, vol. 58, (Aug. 1, 1998),3429-3434.

Virmani, Arvind K., et al., "Promoter Methylation and Silencing of the Retinoic Acid Receptor-B Gene in Lung Carcinomas", *Journal of the National Cancer Institute*, vol. 92, No. 16, (Aug. 16, 2000),1303-1307.

Ylitalo, Nathalie , et al., "Detection of Genital Human Papillomavirus by Single-Tube Nested PCR and Type-Specific Oligonucleotide Hybridization", *Journal of Clinical Microbiology*, (Jul. 1995),1822-1828.

Mullis, Kary B., et al., "Specific Synthesis of DNA in Vitro via a Polymerase-Catalyzed Chain Reaction", *Methods in Enzymology*, vol. 155, (1987),335-350.

\* cited by examiner

Methylation of the p16 and MGMT Genes in Tumor/Sputum Pairs at Time of Diagnosis

| Case | Exposure | Sample | Cytology | Methylation p16 | MGMT |
|---|---|---|---|---|---|
| 1 | Tob/Radon | SCC | NA | M | U |
|   |           | Sputum | Mild Atypia | M | U |
| 2 | Tob/Radon | SCC | NA | U | M |
|   |           | Sputum | SCC | U | M |
| 3 | Tob/Radon | SCC | NA | U | M |
|   |           | Sputum | SCC | U | M |
| 4 | Tob | SCC | NA | M | M |
|   |     | Sputum | SCC | M | U |
| 5 | Tob | SCC | NA | M | M |
|   |     | Sputum | SCC | M | U |
| 6 | Tob/Radon | SCC | NA | M | U |
|   |           | Sputum | Mod. Dyspl. | M | U |
| 7 | Tob | SCC | NA | M | M |
|   |     | Sputum | Marked Dyspl. | M | M |
| 8 | Tob | SCC | NA | M | U |
|   |     | Sputum | Mod. Dyspl. | M | M |
| 9 | Tob | SCC | NA | M | U |
|   |     | Sputum | Mod. Dyspl. | M | U |
| 10 | Tob/Radon | SCC | NA | M | M |
|    |           | Sputum | Marked Dyspl. | M | M |

Methylation state of the p16 and MGMT genes in tumors and sputums obtained at the time of diagnosis. Abbreviations: Tob, tobacco; SCC, squamous cell carcinoma; NA, not applicable; M, methylated; U, unmethylated; Mod Dyspl., moderate dysplasia.

FIGURE 1

Methylation of the p16 and MGMT Genes in Sputum Precedes Clinical Diagnosis of SCC

| Case | Exposure | Sample | Months Prior To Cancer | Cytology | Methylation p16 | MGMT |
|---|---|---|---|---|---|---|
| 1 | Tob/Radon | SCC | 0 | NA | U | M |
|   |   | Sputum | 5 | Mod. Dysp. | M | M |
| 2 | Tob/Radon | SCC | 0 | NA | M | M |
|   |   | Sputum | 5 | Suspicious | M | M |
|   |   | Sputum | 5 | Suspicious | M | M |
|   |   | Sputum | 5 | Marked Dysp. | M | M |
| 3 | Tob | SCC | 0 | NA | M | M |
|   |   | Sputum | 6 | SCC | M | M |
| 4 | Tob/Radon | SCC | 0 | NA | M | U |
|   |   | Sputum | 10 | Mod. Dysp. | M | U |
| 5 | Tob/Radon | SCC | 0 | NA | M | M |
|   |   | Sputum | 8 | Suspicious | M | M |
|   |   | Sputum | 13 | Suspicious | M | M |
| 6 | Tob/Radon | SCC | 0 | NA | M | M |
|   |   | Sputum | 2 | SCC | M | M |
|   |   | Sputum | 9 | Mod. Dysp. | M | M |
|   |   | Sputum | 15 | Mild Atypia | M | U |
| 7 | Tob/Radon | SCC | 0 | NA | M | M |
|   |   | Sputum | 5 | Mod. Dysp. | M | M |
|   |   | Sputum | 15 | Mod. Dysp. | M | M |
| 8 | Tob/Radon | SCC | 0 | NA | M | M |
|   |   | Sputum | 8 | Suspicious | M | M |
|   |   | Sputum | 20 | Suspicious | M | M |
| 9 | Tob/Radon | SCC | 0 | NA | M | U |
|   |   | Sputum | 0 | SCC | M | U |
|   |   | Sputum | 20 | CIS | M | U |
| 10 | Tob | SCC | 0 | NA | M | M |
|   |   | Sputum | 34 | Severe Dysp. | M | U |
| 11 | Tob | SCC | 0 | NA | M | M |
|   |   | Sputum | 35 | Severe Dysp. | M | U |

Methylation state of the p16 and MGMT genes in tumors and sputums obtained from 11 different cases. Abbreviations: Tob, tobacco; SCC, squamous cell carcinoma; NA, NA, not applicable:not applicable; M, methylated; U, unmethylated; CIS, carcinoma in situ; Dysp, dysplasia; Suspicious, suspicious for malignancy.

FIGURE 2

STAGE 1 PCR

| Gene | Primers (5'-3') | SEQ ID NO: | Annealing Tm |
|---|---|---|---|
| P16 cyclin dependent kinase inhibitor 4a | GAGGAAGAAAGAGGAGGGGTTG<br>ACAAACCCTCTACCCACCTAAATC | SEQ ID NO:2<br>SEQ ID NO:4 | 60<br>60 |
| O6-methylguanine DNA methyltransferase | GTTTYGGATATGTTGGGATAGTT<br>AACACTTAAAACRCACCTAAAACTC | SEQ ID NO:6<br>SEQ ID NO:8 | 60<br>60 |
| Death-associated protein kinase | GGTTGTTTYGGAGTGTGAGGAGG<br>ACGCTATCGAAAACCGACCATAAAC | SEQ ID NO:10<br>SEQ ID NO:12 | 60<br>60 |
| RAS-associated family 1 gene | GGAGGGAAGGAAGGGTAAGG<br>CAACTCAATAAACTCAAACTCCC | SEQ ID NO:13<br>SEQ ID NO:14 | 60<br>60 |
| H-Cadherin | TTTTTAYGGAAAATATGTTTAGTGTAGT<br>TAAACTCRAAATAACCTCCCTACC | SEQ ID NO:23<br>SEQ ID NO:24 | 60<br>60 |
| Retinoic acid receptor beta | TTTATGYGAGTTGTTTGAGGATTGG<br>AATCCAAATAATCATTTACCATTTTCC | SEQ ID NO:25<br>SEQ ID NO:26 | 60<br>60 |
| Fragile histidine triad | GGTTATTTAGTGGGTATATTTTTAGG<br>RAATCCCCACCCTAAAACCCTC | SEQ ID NO:27<br>SEQ ID NO:28 | 60<br>60 |

STAGE 2 PCR

| Gene | Primers (5'-3') | SEQ ID NO: | Annealing Tm |
|---|---|---|---|
| P16 cyclin dependent kinase inhibitor 4a | GAGGGTGGGGCGGATCGC | SEQ ID NO:29 | 70 |
| | GACCCCGAACCGCGACCG | SEQ ID NO:30 | 70 |
| O6-methylguanine DNA methyltransferase | ACGTTTTGCGTTTCGACGTTC | SEQ ID NO:31 | 68 |
| | ACCCCCCACCCGACGACG | SEQ ID NO:32 | 68 |
| Death-associated protein kinase | ATAGTCGGATCGAGTTAACGTC | SEQ ID NO:33 | 70 |
| | AAAACTAACCGAAACGACGACG | SEQ ID NO:34 | 70 |
| RAS-associated family 1 gene | GGGGGTTTTGCGAGAGCGC | SEQ ID NO:35 | 68 |
| | CCCGATTAAACCCGTACTTCG | SEQ ID NO:36 | 68 |
| H-Cadherin | GAATGAAAACGTCGTCGGGC | SEQ ID NO:37 | 68 |
| | ATCTATCTTCGCCGCCGCG | SEQ ID NO:38 | 68 |
| Retinoic acid receptor beta | GTCGAGAACGCGAGCGATTC | SEQ ID NO:39 | 68 |
| | CGACCAATCCAACCGAAACG | SEQ ID NO:40 | 68 |
| Fragile histidine triad | GGCGGCGTTTCGGTTTCGC | SEQ ID NO:41 | 68 |
| | GCCCCGTAAACGACGCCG | SEQ ID NO:42 | 68 |

FIGURE 6

Summary of selected demographic variables by study group

| Variable | Cases (n = 52) | Controls (n = 89) |
| --- | --- | --- |
| Age (years) | 68 (44, 79)[a] | 67 (45, 81)[a] |
| Gender (% male) | 96 | 99 |
| Ethnicity (%) | | |
|   Caucasian | 67 | 69 |
|   Hispanic | 21 | 27 |
|   African American | 9 | 1 |
|   Native American | 2 | 2 |
| Smoking Status (% Current) | 28 | 32 |
| Smoking, Duration (yrs) | 50 (18, 66)[a] | 36 (3, 64)[a,b] |
| Smoking, Pack Years | 66 (18, 177)[a] | 48 (1, 183)[a,b] |
| Smoking, Time Quit (yrs) | 3 (1, 34)[a] | 20 (1, 42)[a,b] |

Statistical comparisons are between cases and controls.
[a] Median (minimum, maximum).
[b] $p < 0.005$

FIGURE 8

SEQUENCE LISTING

<160> NUMBER OF SEQ ID NOS: 42

<210> SEQ ID NO 1
<211> LENGTH: 20
<212> TYPE: DNA
<213> ORGANISM: Homo sapiens

<400> SEQUENCE: 1
gaagaaagag gagggttgg                                          20

<210> SEQ ID NO 2
<211> LENGTH: 22
<212> TYPE: DNA
<213> ORGANISM: Homo sapiens

<400> SEQUENCE: 2
gaggaagaaa gaggaggggt tg                                      22

<210> SEQ ID NO 3
<211> LENGTH: 20
<212> TYPE: DNA
<213> ORGANISM: Homo sapiens

<400> SEQUENCE: 3
ctacaaaccc tctacccacc                                         20

<210> SEQ ID NO 4
<211> LENGTH: 24

-continued

```
<212> TYPE: DNA
<213> ORGANISM: Homo sapiens

<400> SEQUENCE: 4
acaaaccctc tacccaccta aatc                                              24

<210> SEQ ID NO 5
<211> LENGTH: 18
<212> TYPE: DNA
<213> ORGANISM: Homo sapiens

<400> SEQUENCE: 5
ggatatgttg ggatagtt                                                     18

<210> SEQ ID NO 6
<211> LENGTH: 23
<212> TYPE: DNA
<213> ORGANISM: Homo sapiens

<400> SEQUENCE: 6
gtttyggata tgttgggata gtt                                               23

<210> SEQ ID NO 7
<211> LENGTH: 17
<212> TYPE: DNA
<213> ORGANISM: Homo sapiens

<400> SEQUENCE: 7
ccaaaaaccc caaaccc                                                      17

<210> SEQ ID NO 8
<211> LENGTH: 25
<212> TYPE: DNA
<213> ORGANISM: Homo sapiens

<400> SEQUENCE: 8
aacacttaaa acrcacctaa aactc                                             25

<210> SEQ ID NO 9
<211> LENGTH: 22
<212> TYPE: DNA
<213> ORGANISM: Homo sapiens

<400> SEQUENCE: 9
ggttgtttcg gagtgtgagg ag                                                22

<210> SEQ ID NO 10
<211> LENGTH: 23
<212> TYPE: DNA
<213> ORGANISM: Homo sapiens

<400> SEQUENCE: 10
ggttgtttyg gagtgtgagg agg                                               23

<210> SEQ ID NO 11
<211> LENGTH: 23
<212> TYPE: DNA
<213> ORGANISM: Homo sapiens

<400> SEQUENCE: 11
gctatcgaaa accgaccata aac                                               23

<210> SEQ ID NO 12
```

```
<211> LENGTH: 25
<212> TYPE: DNA
<213> ORGANISM: Homo sapiens

<400> SEQUENCE: 12
acgctatcga aaaccgacca taaac                                    25

<210> SEQ ID NO 13
<211> LENGTH: 20
<212> TYPE: DNA
<213> ORGANISM: Homo sapiens

<400> SEQUENCE: 13
ggagggaagg aagggtaagg                                          20

<210> SEQ ID NO 14
<211> LENGTH: 23
<212> TYPE: DNA
<213> ORGANISM: Homo sapiens

<400> SEQUENCE: 14
caactcaata aactcaaact ccc                                      23

<210> SEQ ID NO 15
<211> LENGTH: 27
<212> TYPE: DNA
<213> ORGANISM: Homo sapiens

<400> SEQUENCE: 15
ggaggatagt tggattgagt taatgtt                                  27

<210> SEQ ID NO 16
<211> LENGTH: 21
<212> TYPE: DNA
<213> ORGANISM: Homo sapiens

<400> SEQUENCE: 16
caaatccctc ccaaacacca a                                        21

<210> SEQ ID NO 17
<211> LENGTH: 22
<212> TYPE: DNA
<213> ORGANISM: Homo sapiens

<400> SEQUENCE: 17
atagtcggat cgagttaacg tc                                       22

<210> SEQ ID NO 18
<211> LENGTH: 22
<212> TYPE: DNA
<213> ORGANISM: Homo sapiens

<400> SEQUENCE: 18
aaaactaacc gaaacgacga cg                                       22

<210> SEQ ID NO 19
<211> LENGTH: 22
<212> TYPE: DNA
<213> ORGANISM: Homo sapiens

<400> SEQUENCE: 19
ggttttgtga gagtgtgttt ag                                       22
```

```
<210> SEQ ID NO 20
<211> LENGTH: 23
<212> TYPE: DNA
<213> ORGANISM: Homo sapiens

<400> SEQUENCE: 20
acactaacaa acacaaacca aac                                              23

<210> SEQ ID NO 21
<211> LENGTH: 19
<212> TYPE: DNA
<213> ORGANISM: Homo sapiens

<400> SEQUENCE: 21
gggggttttg cgagagcgc                                                   19

<210> SEQ ID NO 22
<211> LENGTH: 21
<212> TYPE: DNA
<213> ORGANISM: Homo sapiens

<400> SEQUENCE: 22
cccgattaaa cccgtacttc g                                                21

<210> SEQ ID NO 23
<211> LENGTH: 28
<212> TYPE: DNA
<213> ORGANISM: Homo sapiens

<400> SEQUENCE: 23
tttttaygga aaatatgttt agtgtagt                                         28

<210> SEQ ID NO 24
<211> LENGTH: 24
<212> TYPE: DNA
<213> ORGANISM: Homo sapiens

<400> SEQUENCE: 24
taaactcraa ataacctccc tacc                                             24

<210> SEQ ID NO 25
<211> LENGTH: 25
<212> TYPE: DNA
<213> ORGANISM: Homo sapiens

<400> SEQUENCE: 25
tttatgygag ttgtttgagg attgg                                            25

<210> SEQ ID NO 26
<211> LENGTH: 27
<212> TYPE: DNA
<213> ORGANISM: Homo sapiens

<400> SEQUENCE: 26
aatccaaata atcatttacc attttcc                                          27

<210> SEQ ID NO 27
<211> LENGTH: 26
<212> TYPE: DNA
<213> ORGANISM: Homo sapiens

<400> SEQUENCE: 27
ggttatttag tgggtatatt tttagg                                           26
```

```
<210> SEQ ID NO 28
<211> LENGTH: 22
<212> TYPE: DNA
<213> ORGANISM: Homo sapiens

<400> SEQUENCE: 28
raatccccac cctaaaaccc tc                                              22

<210> SEQ ID NO 29
<211> LENGTH: 18
<212> TYPE: DNA
<213> ORGANISM: Homo sapiens

<400> SEQUENCE: 29
gagggtgggg cggatcgc                                                   18

<210> SEQ ID NO 30
<211> LENGTH: 18
<212> TYPE: DNA
<213> ORGANISM: Homo sapiens

<400> SEQUENCE: 30
gaccccgaac cgcgaccg                                                   18

<210> SEQ ID NO 31
<211> LENGTH: 21
<212> TYPE: DNA
<213> ORGANISM: Homo sapiens

<400> SEQUENCE: 31
acgttttgcg tttcgacgtt c                                               21

<210> SEQ ID NO 32
<211> LENGTH: 18
<212> TYPE: DNA
<213> ORGANISM: Homo sapiens

<400> SEQUENCE: 32 acccccacc cgacgacg                                                    18

<210> SEQ ID NO 33
<211> LENGTH: 22
<212> TYPE: DNA
<213> ORGANISM: Homo sapiens

<400> SEQUENCE: 33
atagtcggat cgagttaacg tc                                              22

<210> SEQ ID NO 34
<211> LENGTH: 22
<212> TYPE: DNA
<213> ORGANISM: Homo sapiens

<400> SEQUENCE: 34
aaaactaacc gaaacgacga cg                                              22

<210> SEQ ID NO 35
<211> LENGTH: 19
<212> TYPE: DNA
<213> ORGANISM: Homo sapiens

<400> SEQUENCE: 35
gggggttttg cgagagcgc                                                  19
```

```
<210> SEQ ID NO 36
<211> LENGTH: 21
<212> TYPE: DNA
<213> ORGANISM: Homo sapiens

<400> SEQUENCE: 36
cccgattaaa cccgtacttc g                                              21

<210> SEQ ID NO 37
<211> LENGTH: 20
<212> TYPE: DNA
<213> ORGANISM: Homo sapiens

<400> SEQUENCE: 37
gaatgaaaac gtcgtcgggc                                                20

<210> SEQ ID NO 38
<211> LENGTH: 19
<212> TYPE: DNA
<213> ORGANISM: Homo sapiens

<400> SEQUENCE: 38
atctatcttc gccgccgcg                                                 19

<210> SEQ ID NO 39
<211> LENGTH: 20
<212> TYPE: DNA
<213> ORGANISM: Homo sapiens

<400> SEQUENCE: 39
gtcgagaacg cgagcgattc                                                20

<210> SEQ ID NO 40
<211> LENGTH: 20
<212> TYPE: DNA
<213> ORGANISM: Homo sapiens

<400> SEQUENCE: 40
cgaccaatcc aaccgaaacg                                                20

<210> SEQ ID NO 41
<211> LENGTH: 19
<212> TYPE: DNA
<213> ORGANISM: Homo sapiens

<400> SEQUENCE: 41
ggcggcgttt cggtttcgc                                                 19

<210> SEQ ID NO 42
<211> LENGTH: 18
<212> TYPE: DNA
<213> ORGANISM: Homo sapiens

<400> SEQUENCE: 42
gccccgtaaa cgacgccg                                                  18
```

NESTED METHYLATION-SPECIFIC POLYMERASE CHAIN REACTION CANCER DETECTION METHOD

CROSS-REFERENCE TO RELATED APPLICATIONS

This application is a continuation-in-part application of U.S. patent application Ser. No. 60/228,057, entitled "Nested Methylation Specific Polymerase Chain Reaction", to Belinsky, et al., filed on Aug. 25, 2000, and the specification thereof is incorporated herein by reference.

GOVERNMENT RIGHTS

The Government has certain rights to this invention pursuant to National Institutes of Health Grants 50 CA8184 and RO1 CA70190, and pursuant to Cooperative Agreement DE-FC04-96AL76406 and Contract DE-FG02-90ER60939 with the Office of Biological and Environment Research, U.S. Department of Energy.

BACKGROUND OF THE INVENTION

1. Field of the Invention

The present invention relates to cancer detection, specifically a methylation specific polymerase chain reaction method for detecting the presence of gene-specific promoter methylation in tumor cells, and more specifically a nested, two-stage polymerase chain reaction method for amplifying the gene that may be altered in a particular cancer, thereby permitting cancer detection and monitoring by detecting gene inactivation in biological fluids such as sputum and blood. The invention may also find application in the field of pharmacogenomics.

2. Background Art

Cancer is one of the leading causes of death in the U.S. The high mortality from this disease stems from the inability in many cases to detect the cancer at a stage where it can be removed surgically and has not metastasized to other sites in the body. Current radio- and chemotherapy often result in disease remission, but actual cures (long-term term survival) are rare for advanced stage cancer. However, 5-year survival for cancers that are surgically removed with no evidence of distant disease is 60% to 80%. The development of biomarkers usable for early detection, to follow therapy, and to predict outcome of the disease, could greatly aid in managing cancer and increasing long-term survival.

Chemoprevention studies in current and former cancer-free subjects have largely been focused on the effect of defined interventions on cytologic and genetic changes in bronchial epithelium obtained through biopsy. This approach is predicated on the fact that virtually the entire lower respiratory tract is exposed to inhaled carcinogens within cigarette smoke. The resulting "field cancerization" involves the generation of multiple, independently initiated sites throughout the lungs of persons with a long history of smoking. Cytological and genetic changes have been detected throughout the bronchial tree. Many of the genetic changes detected in the bronchial epithelium may have limited utility for assessing lung cancer risk and response to intervention therapy. For example, assays for loss of heterozygosity (LOH) in cytologically normal tissue have limited sensitivity, and quite often subjects will not be informative for the microsatellite marker used to assess LOH at a specific chromosome locus. Moreover, some LOH changes appear less frequently in former smokers compared to current smokers, suggesting they may be associated more with exposure. In addition, the conduct of large population-based prevention trials will necessitate the use of biological fluids such as sputum that can be obtained non-invasively for monitoring drug response. Neither polymerase chain reaction-nor fluorescent in situ hybridization (FISH)-based assays have the sensitivity to detect LOH in sputum. At present, there is no extensive data on methylation in the bronchial epithelium in either persons with prevalent lung cancer or cancer-free smokers. Still further, the effect of smoking cessation on these markers has not been evaluated.

The development of cancer involves inactivation of many different types of genes in a cell. It is this inactivation that is largely responsible for a normal cell becoming a tumor cell. One type of gene inactivation that occurs frequently in cancer is called CpG island methylation of gene promoters. This process involves a change in the portion of the gene, the promoter, which is responsible for maintaining its activity. CpG island methylation is responsible for inactivating many different cellular genes.

Because current and even former cigarette smokers have increased bronchial secretions that contain exfoliated cells from the bronchial tree, the analysis of sputum from these individuals has been an area of research for marker development. The late Dr. Geno Saccomanno demonstrated that premalignant cytologic changes can be detected several years prior to a clinical diagnosis of lung cancer in high-risk subjects. Unfortunately, these studies were difficult to replicate, most likely because of the skills required for identifying subtle nuclear changes in cells that often comprise <5% of the sputum slide. Subsequent studies suggested that molecular assays could be used to enhance the predictive value of sputum samples. Mutations within the K-ras gene have been detected in sputum specimens collected prior to tumor resection; identical microsatellite alterations have been detected in primary tumors and corresponding sputum samples. However, the known methods to detect both alterations lack sensitivity, and the overall prevalence of these changes in non-small cell lung cancer (NSCLC) is less than 25%.

Recently, Drs. James Herman and Stephen Baylin developed a technique, called methylation specific polymerase chain reaction (MSP), to detect the presence of gene-specific promoter methylation in tumor cells. This technique is described in U.S. Pat. No. 5,786,146 to Baylin et al., and U.S. Pat. No. 6,017,704 to Herman, et al., the teachings of which are incorporated herein by reference. With the MSP approach, it is possible to detect one copy of a specific methylated gene in the background of 1,000 unmethylated gene copies. This approach is useful for detection of specific methylated genes in primary tumors, but has extremely limited utility for detecting gene inactivation in biological fluids such as sputum, plasma, urine, and fecal stool. Evaluating biological fluids is the most noninvasive and economical approach for population-based screening. Because these fluids contain DNA or cells that are mainly normal cells, increased sensitivity of the MSP procedure is essential for detecting the presence of the tumor cells.

Against the foregoing background, the present invention was developed.

SUMMARY OF THE INVENTION (DISCLOSURE OF THE INVENTION)

Broadly described, the invention is a nested, two-stage polymerase chain reaction (PCR) method for the monitoring and/or early detection of cancer. The method first expands the number of specific gene copies by using PCR to amplify the gene that may be altered in a particular cancer. This amplification includes the portion of the gene where the promoter methylation resides. At this point, an aliquot of the specific gene amplification product generated through the first PCR is used in a second PCR. The second PCR is methylation-specific, and may utilize the methylation-specific technology of U.S. Pat. No. 6,017,704 to detect the presence or absence of inactivation for that specific gene. Using this inventive nested, two-stage MSP method, the sensitivity for detecting methylation is increased by 50-fold to offer practical utility. The inventive method has been successfully applied to the detection of cancer through monitoring of sputum.

Two of the genes that have been evaluated are the p16 gene and the O6-methylguanine-DNA methyltransferase (MGMT) gene. Both are inactivated through CpG island methylation of their promoters. A "CpG island" is a stretch of DNA that can range in size from about 200 to about 1000 base pairs, with an average percent of G+C over 50%, and an observed/expected CpG ratio above 0.6. DNAs isolated from biological fluids such as sputum or plasma are subjected to bisulfite modification, and PCR is performed to amplify a 280 base pair and 289 base pair fragment of the p16 and MGMT genes, respectively, including a portion of their CpG rich promoter region. "CpG rich" means that the density of cytosine-guanosine runs is denser than normally expected. This first step of the method is central to the improved sensitivity for the inventive procedure. Specific PCR primers (small sequences of DNA bases that are complementary to a specific gene, like p16) are designed to amplify through PCR the gene fragments. Following this amplification, an aliquot of the PCR products that are generated, containing the p16 or MGMT gene fragments, is subjected to a second PCR. Primers specific to methylated DNA regions (only recognized methylated gene fragments—this is the MSP step) are employed to determine whether the gene promoter (p16 or MGMT) is methylated. If a gene promoter is methylated, inactivation is assumed to occur.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the figures:

FIG. 1 is a table setting forth the methylation of p16 and MGMT genes in tumor/sputum pairs at time of diagnosis. In the table, Tob is the abbreviation for tobacco, SCC is the abbreviation of squamous cell carcinoma, M is the abbreviation of methylated, U is the abbreviation of unmethylated, and Mod. Dyspl. is the abbreviation of moderate dysplasia.

FIG. 2 is a table setting forth the methylation of the p16 and MGMT genes in sputum preceding clinical diagnosis of squamous cell carcinoma. In the table, Tob is the abbreviation for tobacco, SCC is the abbreviation of squamous cell carcinoma, M is the abbreviation of methylated, U is the abbreviation of unmethylated, CIS is the abbreviation of carcinoma in situ, Dyspl. is the abbreviation of dysplasia, and Suspicious means suspicious for malignancy.

FIG. 5 is a table setting forth the genes, methylation specific polymerase chain reaction primers, and annealing temperatures (° C.) employed to run the first stage reaction according to one preferred embodiment of the invention.

FIG. 6 is a table setting forth the genes, methylation specific polymerase chain reaction primers, and annealing temperatures (° C.) employed to run the second stage reaction according to one preferred embodiment of the invention.

FIG. 8 is a table summarizing selected demographic variables, by study group, of cases and controls involved in an exemplar test demonstrative of the invention.

Figure 3:
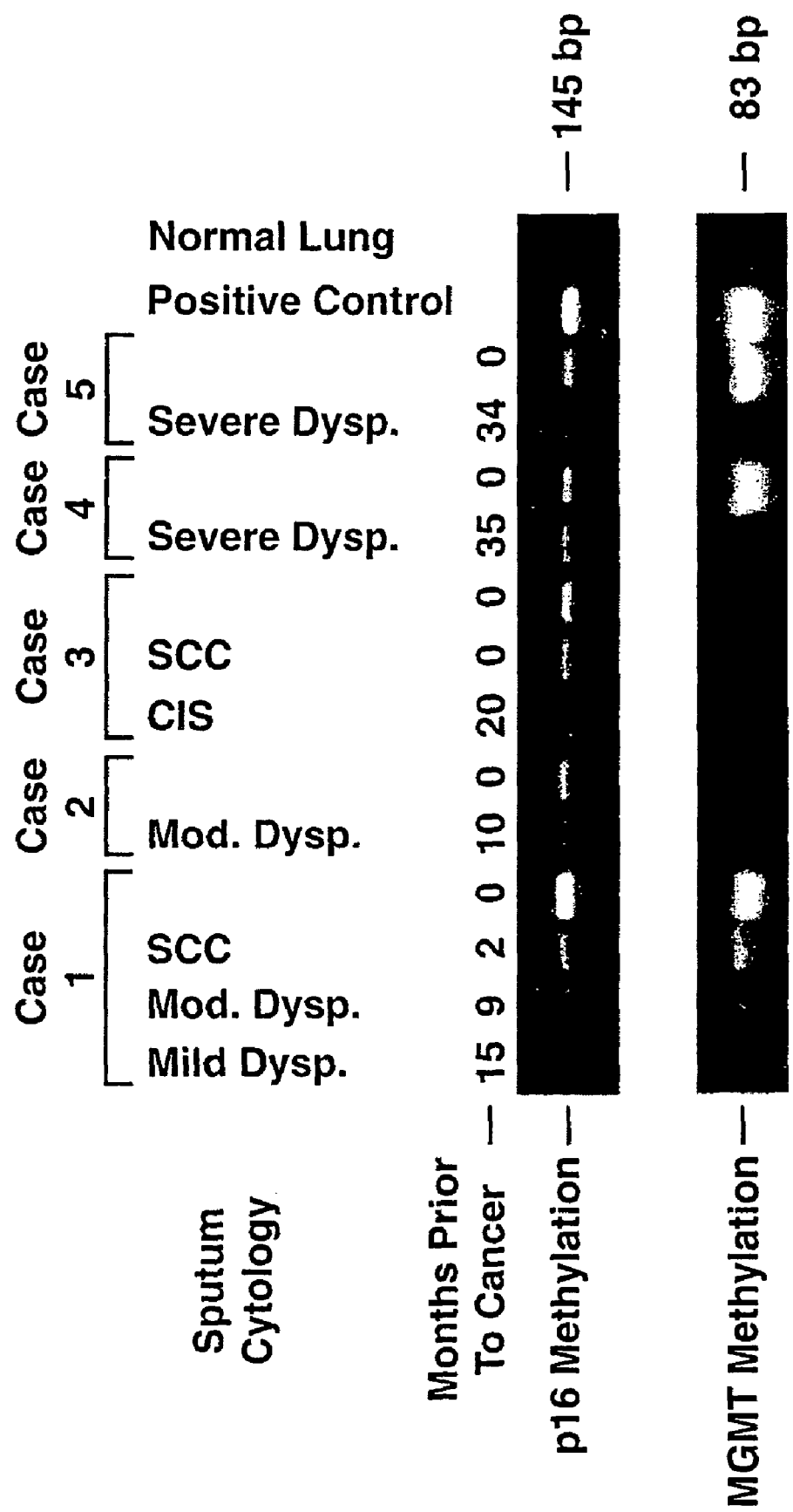
FIG. 3 is a diagram showing that P16 and MGMT methylation in sputum are biomarkers for squamous cell carcinoma, depicting results of the stage-2 PCR using methylation-specific primers for the p16 and MGMT gene. Sputum (samples collected months prior to cancer) and primary SCC (time zero) are shown for five cases. The presence of 145 bp and 83 bp PCR products indicate that the sputum or tumor was positive for p16 and MGMT methylation, respectively. The CaLu6 and SKuLu1 cell lines are the positive controls for p16 and MGMT methylation, respectively, and normal lung served as a negative control. Sputum cytology varied by case and is indicated for each specimen.

DESCRIPTION OF THE PREFERRED EMBODIMENTS (BEST MODES FOR CARRYING OUT THE INVENTION)

Lung cancer is the leading cause of cancer-related death in the U.S. and is projected to reach epidemic levels in the world during the 21st century. Mortality from this disease could be reduced greatly through the development of molecular markers that identify individuals at the earliest stages of lung cancer where curative resection is feasible. Candidate biomarkers should have high sensitivity and specificity, and appear sufficiently early in the course of disease for medical intervention to improve prognosis. Finally, the markers must be present in a biological fluid that can be obtained noninvasively, making its collection feasible for population-based screening.

The present invention provides a molecular-based marker method for the early detection of human cancer, especially lung cancer. The inventive method involves the detection of gene promoter regions that are aberrantly hypermethylated in human tumors. This change is associated with an epigenitically mediated gene silencing that constitutes an alternative to coding region mutations for loss of tumor suppressor gene function in cancer. The applicants have determined that aberrant promoter methylation of the P16 INK4a (p16) tumor suppressor gene, which plays a key role in cell cycle regulation, is an early and very frequent event in squamous cell carcinoma (SCC) of the lung. Another gene frequently inactivated by aberrant promoter methylation in human non-small-cell lung cancer is O 6-methylguanine-DNA methyltransferase (MGMT). MGMT is a DNA repair enzyme that protects cells from the carcinogenic effects of alkylating agents by removing adducts from the O 6 position of guanine. Thus, the p16 and MGMT genes are strong candidate biomarkers for early detection of lung cancer.

That aberrant methylation of the p16 promoter region can be detected in DNA from exfoliated cells in sputum of patients with this disease supports the inventive methodology for the monitoring and early diagnosis of cancer. According to the invention, aberrant methylation of the p16 gene promoter was detected in sputum from three of seven patients with lung cancer, and five of 26 cancer-free individuals at high-risk. The present invention involves a modification, to achieve even higher detection efficiency, of the methylation-specific polymerase chain reaction (PCR) assay used initially. The invention has utility for monitoring purposes irrespective of the physiological state of the cell (e.g. pre-malignancy) and also irrespective of the precise location of the methylated gene. Thus, the inventive method is used to extend not only analysis of the p16 promoter, but to study the methylation status of a similar region of MGMT or other specific and particular genes that may be altered by diseases such as cancer. Aberrant methylation of one of these two promoter regions was detected in sputum of 100% of patients with proven SCC, not only at the time of diagnosis, but also in all sputum samples taken from patients five to 35 months prior to clinical tumor detection. Furthermore, these sputum markers were detected in a subset of cancer-free individuals with very high risk for developing lung tumors. Detection of aberrant promoter region methylation is central to the inventive approach for using DNA-based markers for the early detection of lung and other common human cancers.

Applicants have identified several biomarkers with great potential for the early detection of a common, non-inherited, cancer. Using two markers, which are frequent in non-small cell lung tumors, a perfect record for detecting a DNA methylation abnormality in sputum up to three years prior to clinical diagnosis of SCC was obtained in a group of patients. With these two biomarkers, 100% of SCCs also were detected through analysis of sputum collected at the time of clinical diagnosis. This conclusion is supported by applicants' finding of p16 and MGMT methylation in cancer-free, high-risk subjects at prevalences that approximate lifetime risk for lung cancer. Thus, aberrant gene methylation is a useful molecular marker approach to population-based screening for detecting lung cancer and monitoring the efficiency of chemopreventative agents. Furthermore, in these individuals, sputum samples were positive in both patients in this cohort who developed SCC to date.

The inventive biomarker approach also aids the sensitivity and accuracy of other diagnostic approaches for lung cancer that are currently receiving much attention. For example, the spiral computerized tomography (spiral CT) imaging procedure can detect very small peripheral lung cancers where routine chest X-rays are negative. However, in terms of the actual presence of lung cancer, many false positive results are the rule, and actual cancer detection rates using spiral CT are currently 0.3% to 0.48%. This scanning diagnostic approach might be enhanced by combining it with the determination of hypermethylation biomarkers in the sputum according the present invention.

Patients with Stage-I or -II disease have a 5-year cure rate of 60% to 80%, whereas Stage III patients have a median survival of 13 months. Lung cancer rates could be reduced by the development of a cost-effective screening approach according to the invention. Key to any screening approach is the identification of markers of lung cancer that can be detected through sensitive and specific diagnostic assays. It is clear that mutation of the K-ras and p53 genes and microsatellite instability constitute alterations important for lung carcinogenesis. However, current methods for examining the concordance of detecting these changes in bronchoalveolar lavage fluid from patients with early stage lung cancer show limited sensitivity.

The inventive method improves upon all previous efforts by incorporating a nested, two-stage PCR approach, which is highly sensitive (one methylated allele in >50,000 unmethylated alleles). Due to the inherent difficulties (e.g., DNA degradation) of assaying for methylation in DNA recovered from fixed tissues, previous efforts and studies have likely underestimated the actual frequency of methylation. In the development of the invention, the applicants observed a strong correlation between loss of expression of both p16 and MGMT and methylation.

The present invention also accounts for detecting at least one methylation marker in both sputum and corresponding tumor from every patient at the time of tumor diagnosis or within 3 years of tumor diagnosis. This contrasts with the applicants' previous study, where using only the one-stage PCR approach, p16 methylation was detected in sputum from 43% of lung cancer cases. (Belinsky, S. A., et al., "Aberrant methylation of p16 is an early event in lung cancer and a potential biomarker for early diagnosis." Proc. Nat'l Acad. Sciences USA), 95:11891-11896 (1998).) There were a few instances in which there were discordant findings for one of the two markers. In each case, the other marker allowed for a positive sputum change to correlate with presence of a cancer, or the development of one, within three years or less.

Possible explanations exist for the instances in which a positive marker was found in the sputum but not in the corresponding tumor. First, the presence of promoter hypermethylation for a given gene can be heterogeneous within a tumor, and sampling would then determine whether it is detected or not. Second, the cancer may arise within a widespread process of bronchial epithelial changes, or so-called "field cancerization" in which cells have a very high risk for malignant transformation. The applicants have detected p16 methylation in non-malignant bronchial epithelial cells from different lung lobes of the same patient with a defined lung cancer, and such high-risk cell populations could contribute exfoliated cells that contain a hypermethylation marker to the sputum. Referring to FIG. 2, and specifically Cases 10 and 11 thereof, the finding that MGMT methylation was not present in two sputum samples collected 3 years prior to clinical diagnosis may be related to the timing for inactivation of this gene in those tumors. Similarly, with reference to FIG. 1 (Case 6), MGMT methylation was not seen in the sputum sample collected 15 months prior to cancer, but was present at 9 months.

Inactivation of genes by methylation is a major mechanism in cancer. Hypermethylation-associated inactivation of p16 is an early and frequent event in non-small-cell lung cancers (NSCLCs) (SCC: 60% to 80%; adenocarcinoma: 30 to 45%) and other cancers. In experimental systems, such loss appears to act as a "gate keeper" in permitting cells to pass through early steps of cellular immortalization. The invention therefore can find application in the area of chemoprevention, where markers are needed to identify high-risk subjects and to evaluate efficacy of preventive agents.

The nested, two-stage PCR approach was utilized, which improved the sensitivity (one methylated allele in >50,000 unmethylated alleles) to detect methylated alleles by over 50-fold over known MSP methods. DNAs were subjected to bisulfite modification, and PCR was performed to amplify a 280 base pair and 289 base pair fragment of the p16 and MGMT genes, respectively, including a portion of their CpG rich promoter region. The primers recognize the bisulfite-modified template, but do not discriminate between methylated and unmethylated alleles.

The stage-1 PCR products were diluted 50-fold, and 5 µl of the product was subjected to a stage-2 PCR in which primers specific to methylated or unmethylated template were used. Primer sequences used in the "stage 1" amplification of the p16 and MGMT genes are as follows:

```
p16-Forward,   5'-GAAGAAAGAGGAGGGGTTGG-3', (SEQ ID NO:1);
p16-Reverse,   5'-CTACAAACCCTCTAC CCACC-3', (SEQ ID NO:3);
MGMT-Forward,  5'-GGATATGTTGGGATAGTT-3', (SEQ ID NO:5); and
MGMT-Reverse,  5'-CCAAAAACCCCAAACCC-3' (SEQ ID NO:7).
```

EXAMPLE ONE

Sputum samples and matched SCCs were obtained from 21 people previously enrolled in a Lung Cancer Surveillance Study conducted through St Mary's Hospital, Grand Junction, Colo. The SCCs were obtained through biopsy or surgical resection. Sputum was collected by standardized procedures at Johns Hopkins Medical Institutions. Sputum was collected from 32 patients being evaluated for possible lung cancer through referral from their primary care physician, and from 91 cancer-free, former uranium miners from Grants, N. Mex., participating in a cancer surveillance study. The study was approved by the respective Institutional Review Boards; all participants gave written informed consent.

Sputum was considered unsatisfactory for evaluation if alveolar lung macrophages were absent or if a marked inflammatory component was present that diluted the concentration of pulmonary epithelial cells.

SCC tumors were obtained as frozen or formalin-fixed specimens. Frozen tumors were not microdissected. Sequential sections (5 µm) were prepared from tumors or biopsies, deparafinized, and stained with toluidine blue to facilitate dissection. A 25-gauge needle attached to a tuberculin syringe was used to remove the lesions under a dissecting microscope. Because some SCCs are extensively contaminated with normal tissue or very small in size (the situation for the biopsy), it was essential to include normal-appearing cells to ensure that after bisulfite modification and column clean-up of the DNA template, enough sample remained to conduct the MSP assay as described below. Thus, because the goal of the process was to determine whether p16 methylation was present microdissection was used to enrich the samples examined.

DNA was isolated from frozen tumors, microdissected tumors, and sputum by digestion with Pronase in sodium dodecyl sulfate (1%), followed by standard phenol-chloroform extraction and ethanol precipitation.

The methylation status of the p16 and MGMT genes was then determined by the inventive modified MSP method. TaqTM Gold polymerase (Perkin Elmer) in a 50 µl volume was used in all PCRs. The PCR amplification protocol for stage 1 was as follows: 95 degrees C. for 10 minutes, then denature at 95 degrees C. for 30 seconds, anneal at 60 degrees C. (for p16) or 52 degrees C. (for MGMT) for 30 seconds, extension at 72 degrees C. for 30 seconds for 40 cycles, followed by a 10 minute final extension.

Primers suitable to selectively amplify unmethylated or methylated alleles of the p16 and MGMT genes in the second, or "stage 2," PCR have been described previously in the art. (Esteller, M., et al., "Inactivation of the DNA repair gene O6-methylguaine-DNA methyltransferase by promoter hypermethylation is a common event in primary human neoplasia." Cancer Res., 59:793–797 (1999); Herman, J. G., et al., "MSP: a novel PCR assay for methylation status of CpG islands." Proc. Nat'l Acad. Sciences (USA), 93:9821–9826 (1996).) Annealing temperatures for the second PCR were increased to 70 degrees C. (for p16) and 62 degrees C. (for MGMT), and all cycling times reduced to 15 seconds for a total of 40 cycles. Normal human tissue collected from autopsy of never smokers, and cell lines positive for p16 (Calu6) and MGMT (SkuLu1) methylation, served as negative and positive controls. All assays were conducted in at least duplicate. (Sensitivity for detecting methylated alleles was determined by mixing DNA isolated from either Calu6 or SkuLu1 cells with DNA isolated from lung tissue of a never smoker to achieve dilutions up to 1 in 100,000. The mixed DNA sample was then subjected to bisulfite modification and subsequent analysis by the two-stage MSP approach.)

Sputum samples that rendered positive methylation products were also analyzed by a second method using restriction enzyme digestion of the resulting PCR product. Second-stage PCRs were performed in duplicate for each sample. Then one of each sample pair was incubated with the restriction enzyme FNU 4HI that cuts (G/CGGCG) at two sites within the amplified region of the methylated p16 gene promoter. (That is, the restriction enzyme is employed after the second stage PCR) The restriction enzyme only cuts template that is methylated at the two CpG sites, since the unmethylated cytosines would be modified by the bisulfite treatment to uracils. Since FNU 4HI cuts at two different sites within the promoter, applicants confirmed that four CpGs were methylated, which verified the methylation status of the sample. Thus, by using a selected restriction enzyme, one is able to quantify, to a certain extent, the number of different methylated gene sites.

An identical approach was used for the MGMT gene using the Taq 1 and BstU1 restriction enzymes to assay three different CpG sites. All sputum samples scored as positive for methylation were confirmed by both procedures.

Statistical comparisons were then done by Fisher's Exact test. Aberrant methylation of p16 and/or MGMT is detected in the sputum of all tested lung cancer patients at the time of diagnosis. Sputum samples and matched SCCs were obtained from 21 people previously enrolled in a Lung Cancer Surveillance Study conducted through St Mary's Hospital, Grand Junction, Colo. All subjects had a history of smoking, and approximately 50% were exposed to radon through uranium mining at the Colorado Plateau. (At sufficiently high concentrations, radon (222Ra) and the associated α-particle-emitting decay products polonium-214 and -218, cause an excess of lung cancers in smokers who mined uranium.) Sputum was collected from 10 of the above 21 individuals at the time of diagnosis of SCC; as seen in FIG. 1, only four samples were diagnostic of cancer by cytologic criteria. In marked contrast to cytology findings, one or both gene promoters tested were abnormally methylated in all of these sputum samples. Continuing reference to FIG. 1 shows that abnormal p16 gene methylation was present in sputum from all eight patients whose tumors were also positive for this marker, but not in sputum from the two individuals whose tumors were negative for this change. Four of the six patients with abnormal methylation of MGMT in their tumors also had this change detected in their sputum, including the two patients whose tumors lacked the p16 change. As indicated by Cases 4 and 5 in FIG. 1, methylation of p16 was present in sputum of the two individuals whose sputum was negative for MGMT. Aberrant MGMT methylation was not detected in sputum or tumor from three cases. In Case 8 of FIG. 1, MGMT methylation was detected in the sputum, but not in the tumor.

The foregoing disclosure indicates that the detection of p16 and MGMT promoter methylation precedes clinical cancer. Reference is made to FIG. 2. For the other 11 of 21 original individuals with SCC, sputum samples were obtained well before the diagnosis of SCC at times ranging from 5 to 35 months. In only one patient (FIG. 2, Case 3) was the sputum sample thought to have unequivocal signs of cancer by cytologic criteria.

However, abnormal methylation of the p16 promoter region was detected in DNA from sputum of all 11 subjects with the longest time to tumor diagnosis being 35 months. With continued reference to FIG. 2, where multiple sputum samples were available either as replicate specimens (Case 2), or as temporal samples (e.g. Case 6), methylation of p16 was always present. A 90% concordance was also observed between p16 methylation in the primary SCC and paired sputum samples, as indicated by FIGS. 2 and 3. FIG. 3 shows the results of the stage-2 PCR using methylation-specific primers for the p16 and MGMT gene. Sputum (samples collected months prior to cancer) and primary SCC (time zero) are shown for five cases. The presence of a 145 bp and 83 bp PCR products indicate that the sputum was positive for p16 and MGMT methylation, respectively. The CaLu6 and SKuLu1 cell lines are the positive controls for p16 and MGMT methylation, respectively, and normal lung served as a negative control. Sputum cytology varied by case and is indicated in FIG. 3 for each specimen. Sputum from seven of 11 cases (FIGS. 1 and 3) also showed methylation of the MGMT gene, as indicated in FIGS. 1 and 3. A 78% concordance was noted between MGMT methylation in the primary SCC and the paired sputum sample. For the two discordant samples, MGMT methylation was detected in the tumor but not in the single sputum sample obtained 34 or 35 months prior to cancer (FIG. 2).

The demonstration of this Example 1 also considered the methylation of p16 and MGMT in cancer-free, high-risk subjects. The excellent concordance between detecting p16 and/or MGMT methylation in sputum samples prior to and at the time of SCC diagnosis warranted defining whether these two markers are present in any sputum samples from cancer-free subjects who are at high risk for lung cancer development. This information is valuable for the ultimate development of risk estimates for lung cancer. Sputum samples were collected from 123 cancer-free subjects. People were divided into three groups based on exposure: 1) tobacco, 2) tobacco plus radon, and 3) radon alone. Approximately 50% of these people were considered heavy smokers with more than 30 pack-year history. Radon exposure ranged from 3 to 577 working level months; 75% of the people had more than 100 working level months. These former uranium miners worked in Grants, N. Mex., where exposures were much lower than in Colorado.

Figure 4:
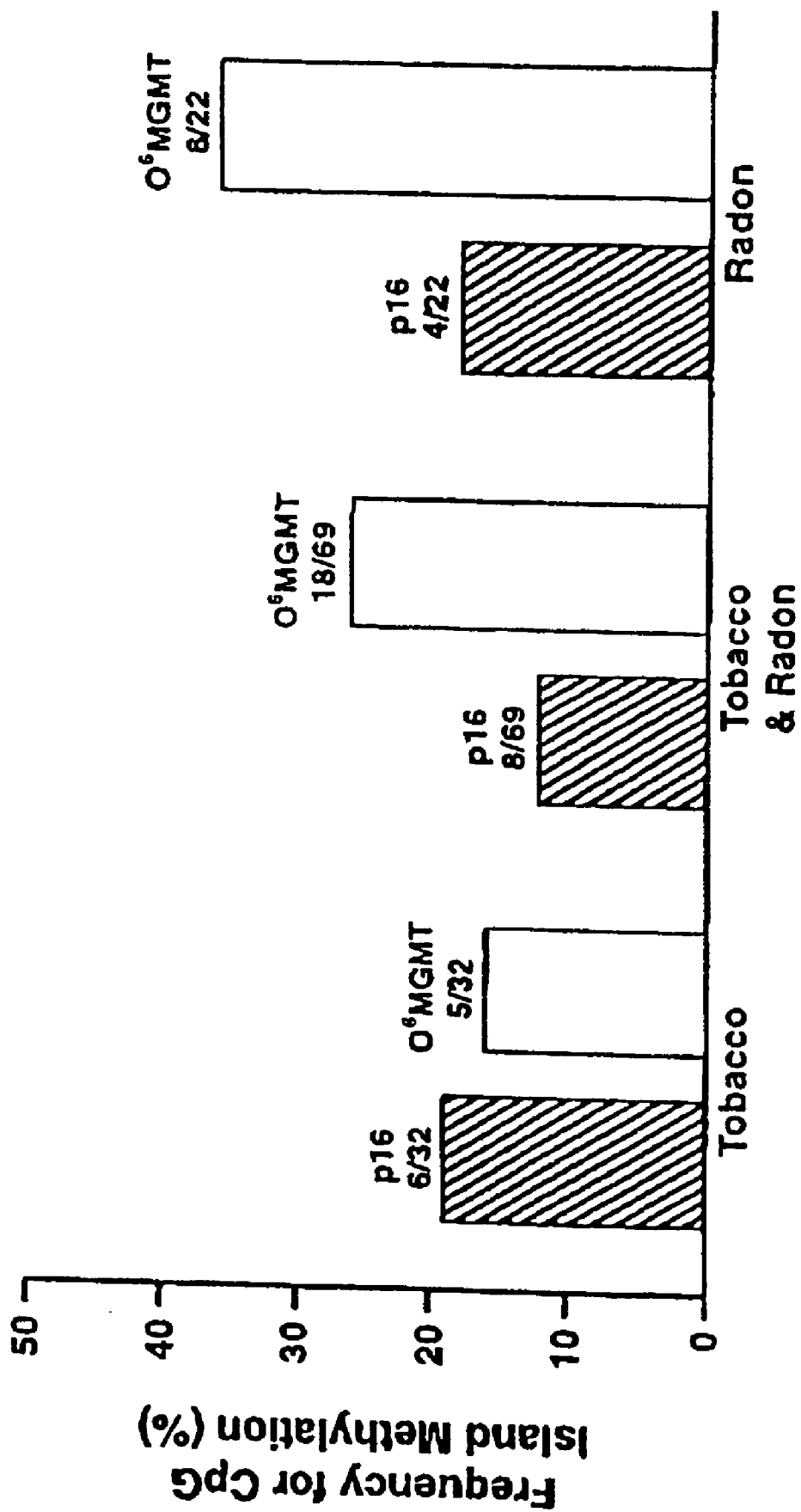
FIG. 4 is a graph showing the prevalence for p16 and MGMT methylation in sputum from cancer-free subjects. The frequency for p16 and MGMT methylation in cancer-free subjects in sputum is expressed as a percentage. Above the bar graphs is indicated the total number of positive samples per total sample population.

FIG. 4 shows the prevalences for p16 and MGMT methylation in sputum from cancer-free subjects. The frequency for p16 and MGMT methylation in cancer-free subjects in sputum is expressed as a percentage. Above the bar graphs of FIG. 4 are indicated the total number of positive samples per total sample population. As seen in FIG. 4, the frequency for detecting aberrant methylation of the p16 or MGMT genes was similar across all groups, occurring in 12–19% and 16–36%, respectively. Smoking status was available for a subset (n=35) of the uranium miners and the methylation markers were present in sputum from both current and former smokers, consistent with the continued risk for lung cancer in former smokers. Bisulfite sequencing of sputum samples (n=5 for each gene) positive for p16 or MGMT revealed methylation at all CpG sites between the PCR primers (not shown).

Furthermore, the examination of DNA isolated from lungs of autopsy cases, bronchial epithelial cells obtained by bronchoscopy, and lymphocytes (a component of the sputum) from never smokers and all were proven negative for the methylation markers (not shown).

Both p16 and MGMT methylation was detected in only four of 123 cancer-free subjects (3%), as opposed to 10 of 21 (48%) of the patients with SCC. The much lower incidence (p<0.001) of detecting both sputum markers in cancer-free subjects than in the 21 individuals studied having proven lung cancer reinforces two determinations. First, hypermethylation changes in sputum DNA do not simply reflect exposure to risk factors for lung cancer, but rather track with either a very high-risk status or actual presence of cancer. Second, the average incidence of –25% for detection of either sputum marker in the cancer-free individuals is approximately equal to the known risk of lung cancer development for the populations studied. This indicates that these hypermethylation markers may potentially identify those patients at high risk who are most likely to actually get the disease.

To date, three lung cancers have been reported in the follow-up on this cancer-free population, which now ranges from two to six years after sputum collection: two in former uranium miners who smoked, and one in a smoker. Eight deaths have occurred not related to lung cancer. Two lung cancers were diagnosed as SCC, one and three years following sputum collection. The MGMT gene was methylated in sputums from both of these subjects. The other tumor was an adenocarcinoma. The incidence of p16 and MGMT hypermethylation is lower in this tumor type as opposed to SCC, and neither marker was present in the sputum sample collected two years prior to diagnosis.

EXAMPLE TWO

Cases (n=52) and controls (n=89) were recruited from veterans who use the New Mexico Veterans Health Care System (NMVHCS) for their primary care. Current or former cigarette smokers (>100 cigarettes smoked during their lifetime) were eligible for the test. In addition, subjects could not have had prior diagnosis of cancer of the aerodigestive tract, have undergone chemotherapy or radiotherapy to the chest within the last year, or be unable to tolerate all procedures required to obtain tissue samples, as further described below.

Cases were recruited from patients referred to the Multispecialty Chest Clinic at NMVHCS, where >90% of the NMVHCS lung cancer cases are evaluated for diagnosis and treatment recommendations. Patients are referred to this clinic because of signs or symptoms suggestive of lung cancer. All patients referred for diagnostic evaluation for lung cancer were recruited for participation in the test. Only those patients with histologic confirmation of lung cancer and who gave consent were enrolled into the study population as cases. All stages and histologic types of lung cancer were included. Controls were enrolled from the population of lung cancer-free individuals who received their primary care at the NMVHCS. Patients were approached randomly during primary-care clinic visits and asked to participate in the study. All subjects were asked to volunteer for a bronchoscopy; however, participation was not dependent on agreeing to this procedure. In addition, patients undergoing bronchoscopy for reasons other than a diagnosis of lung cancer (e.g., interstitial lung disease) were included as controls.

The distribution of tumor histology among the 52 cases was 44% SCC, 31% adenocarcionoma, 2% large cell carcinoma, 8% small cell carcinoma, and 15% NSCLC (subtype not specified). Selected demographic variables by casecontrol status are summarized in the table of FIG. 8. The only significant differences seen between groups were for smoking history where duration and pack years were greater in cases, while years since quit for former smokers were greater in the control group.

All participants enrolled for this study were approached to undergo bronchoscopy. A high proportion (>85%) of cases underwent bronchoscopy since it is performed routinely as a diagnostic or staging procedure in lung cancer patients, and 45% of controls consented to undergo this procedure. Bronchial epithelial cells (BECS) were obtained during bronchoscopy as previously described. BECs were harvested from up to four different sites at anatomically normal appearing bifurcations in the lungs, usually within each upper and lower lobe, using a standard cytology brush. These sites were sampled because: (1) they are high-deposition areas for particles; (2) they are frequently associated with histological changes in smokers; and (3) they represent common sites of tumors. Sites selected for brushing were first washed with saline to remove non-adherent cells. Sites were not brushed if a tumor was visualized within 3 cm of the site. After brushing, the brush was placed in serum-free medium and kept on ice until processed. Up to three brushings were performed at each site. In addition, BECs from never smokers were obtained from two different sources: cells derived at autopsy by Clonetics, Inc. (San Diego, Calif. USA) from four never smokers and cells from three never smokers recruited through the NMVHS.

Tumor tissue was available either by resection or biopsy from 18 persons diagnosed with lung cancer. Tumor tissue was fixed in formalin and embedded in paraffin for subsequent analysis for methylation of the p16 gene.

Cells were flash-frozen in liquid nitrogen for DNA isolation. Cells from one brush from each bronchial collection site were prepared for cytologic analysis by smearing the cells across a microscope slide. The cells were then fixed with 96% ethanol and stained according to the Papanicolaou procedure to facilitate morphologic evaluation by a cytopathologist.

On enrollment, patients were asked to provide an uninduced sputum specimen. If unsuccessful, participants underwent sputum induction. A variation of the ultrasonic nebulization technique described by Saccomanno was used for sputum induction. Subjects used water or saline to gently brush tongue, buccal surfaces, teeth, and gingiva to remove superficial epithelial cells and bacteria, followed by gargling and rinsing with tap water. Patients then inhaled a nebulized 3% saline solution from an ultrasonic nebulizer for 20–30 minutes. Sputum was collected in a sterile specimen cup, and an equal volume of Saccomanno solution was added immediately. Sputum samples were processed for methylation analysis by extensive mixing by vortex, washed once with Saccomanno solution, and stored at room temperature until analyzed. In addition, at least two slides from sputum samples were prepared and underwent Papanicoleau staining for morphologic examination by a certified cytopathologist.

DNA was isolated from BECs, tumors, and sputum by digestion with Pronase in 1% sodium dodecyl sulfate, followed by standard phenol-chloroform extraction and ethanol precipitation.

The methylation status of the p16, MGMT, DAP-kinase, and RASSF1A genes was determined by the inventive method of MSP. Nested, two-stage PCR method was conducted, which improved the sensitivity to detect methylated alleles by >50-fold over the original "one-stage" method (one methylated allele in >50,000 unmethylated alleles). DNAs were subjected to bisulfite modification, and PCR was performed to amplify 280 base pair, 289 base pair, 209 base pair, and 260 base pair fragment of the p16, MGMT, DAP-kinase, and RASSF1A genes, respectively, including a portion of their CpG rich promoter region. The primers recognize the bisulfite-modified template, but do not discriminate between methylated and unmethylated alleles. The stage-1 PCR products were diluted 50-fold, and 5 μl was subjected to a stage-2 PCR in which primers specific to methylated or unmethylated template were used. Primer sequences and conditions used in stage-1 and -2 amplification of the p16 and MGMT promoters have been described. Primer sequences used in the stage-1 amplification of the DAP-kinase and RASSF1A genes are as follows:

```
Dap-kinase-Forward, 5'-GGTTGTTTCGGAGTGTGAGGAG-3', (SEQ ID NO:9);

DAP-Kinase-reverse, 5'-GCTATCGA-AAACCGACCATAAAC-3', (SEQ ID NO:11);

RASSF1A-Forward,    5'-GGAGGGAAGGAAGGGTAAGG-3', (SEQ ID NO:13); and

RASSF1A-Reverse,    5'-CAACTCAATAAACTCAAACTCCC-3' (SEQ ID NO:14).
```

TaqTM Gold polymerase (Perkin Elmer) in a 50-µl volume was used in all PCRs. The PCR amplification protocol for stage 1 was as follows: 95° C. 10 minutes, then denature at 95° C. 30 seconds, anneal at 58° C. (for DAP-kinase) or 60° C. (for RASSF1A) 30 seconds, extension at 72° C. 30 seconds for 40 cycles, followed by a 5-minute final extension. Primers used to selectively amplify unmethylated or methylated alleles of the DAP-kinase gene are as follows:

cytosines would be modified by the bisulfite treatment to uracils. Since FNU 4HI cuts at two different sites within the portion of the p16 promoter being examined, applicants confirmed that four CpGs were methylated, which verified the methylation status of the sample. An identical approach was used for the DAP-kinase and RASSF1A genes using the BstUI restriction enzymes were used to assay three different

```
Forward unmethylated, 5'-GGAGGATAGTTGGATTGAGTTAATGTT-3', (SEQ ID NO:15);

Reverse unmethylated, 5'-CAAATCCCT-CCCAAACACCAA-3', (SEQ ID NO:16);

Forward methylated,   5'-ATAGTCGG-ATCGAGTTAACGTC-3', (SEQ ID NO:17); and

Reverse methylated,   5'-AAAACTAACCGAAA-CGACGACG-3' (SEQ ID NO:18).
```

Primers used to selectively amplify unmethylated or methylated alleles of the RASSF1A gene are forward unmethylated, 5'-GGTTTTGTGAGAGTGTGTTTAG-3'(SEQ ID NO:19), reverse unmethylated, 5'-ACACTAACAAA-CACAAACCAAAC-3'(SEQ ID NO:20), forward methylated, 5'-GGGGGTTTTGCGAGAGCGC-3'(SEQ ID NO:21), and reverse methylated, 5'-CCCGATTAAACCCG-TACTTCG-3'(SEQ ID NO:22), Annealing temperatures were increased to 70° C. and 62° C. (for DAP-kinase) and 68° C. and 62° C. (for RASSF1A) to amplify methylated and unmethylated sequences, respectively, and all cycling times were reduced to 15 seconds for a total of 40 cycles.

It will be immediately understood that other primers besides those specified may be employed without departing from the scope of the invention. The primer sequences can be changed; that is, both the inner primers and the outer primers may be shifted either direction a number of bases, yet within the nested approach of the invention. Modifying the location of one or more primers is a contemplated aspect of the invention within the understanding of a person of ordinary skill in the art.

Product sizes for each gene promoter were as follows: 153 base pairs and 106 base pairs for methylated and unmethylated DAP-kinase; and 204 base pairs and 170 base pairs for methylated and unmethylated FASSF1A. Normal human tissue collected from autopsy of never smokers and cell lines positive for p16 (Calu6), MGMT (SkLU1), DAP-kinase (H2009), and RASSF1A (A549) methylation served as negative and positive controls. These cell lines were purchased from the ATCC (Mansius, Va. USA) and cultured using the suggested protocols.

Samples that gave positive methylation products were also analyzed by methylation-sensitive restriction enzyme digestion of the resulting PCR product. Second-stage PCRs were performed in duplicate for each sample. Then for p16, one of each sample pair was incubated with the restriction enzyme FNU 4HI that cuts (G/CGGCG) at two sites within the amplified region of the methylated p16 gene promoter. Thus, this restriction enzyme will only cut template that is methylated at the two CpG sites, since the unmethylated CpG sites within the MGMT gene. All samples scored as positive for methylation were confirmed by restriction analysis.

Data were summarized using percents for discrete variables and medians with ranges for continuous variables. Differences between groups were assessed using Fisher's exact test for discrete variables and the Wilcoxon rank sum test for continuous variables. Results from pairs of markers were examined using Fisher's exact test to assess the association between markers and MacNemar's test to assess differences in proportions positive for the markers. Logistic regression models with case-control status as the outcome were used to control for multiple predictor variables simultaneously. All analyses were conducted in SAS software (SAS Institute In., Cary, N.C. USA).

Cytologic changes were characterized in BECs obtained from up to four sites in 51 cases (cytology not available for one case) and 41 controls. A total of 166 and 150 sites were evaluated in cases and controls, respectively. Metaplasia (reactive) and mild dysplasia (atypia) were the predominant cytological abnormalities observed, and their distribution did not differ among groups. One case had severe dysplasia within a bronchial epithelial site. Cytologic changes were seen in at least one site in approximately 54% of both cases and controls. The number of cases with at least two or three sites positive for cytology exceeded those observed in controls: 33% versus 20% (p=0.24) and 25% versus 3% (p=0.007), respectively. These cytologic changes were observed in <10% of cells recovered from the diagnostic brush. There was no apparent association between the presence of cytology and tumor histology or smoking status (current versus former); however, cases with cytologic changes in their bronchial epithelium smoked more than those without cytologic changes (median pack years, 78 versus 59; p=0.10).

Figure 9:
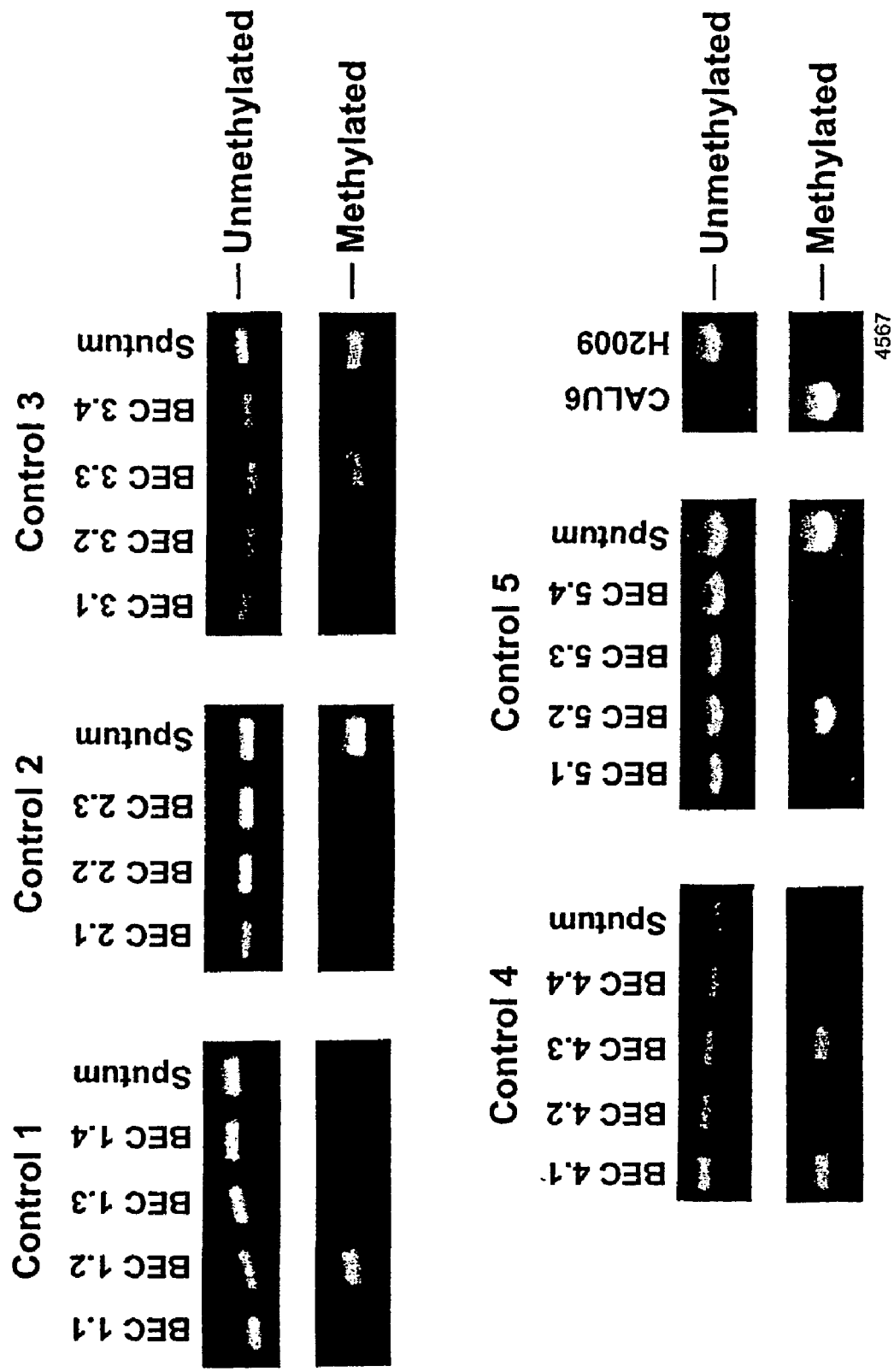
FIG. 9 depicts methylation of the p16 gene in bronchial epithelial cells and corresponding sputum. Representative scenarios for detection of methylation in bronchial epithelial cells and sputum from five different controls involved in an exemplar test demonstrative of the invention are shown
Figure 10:
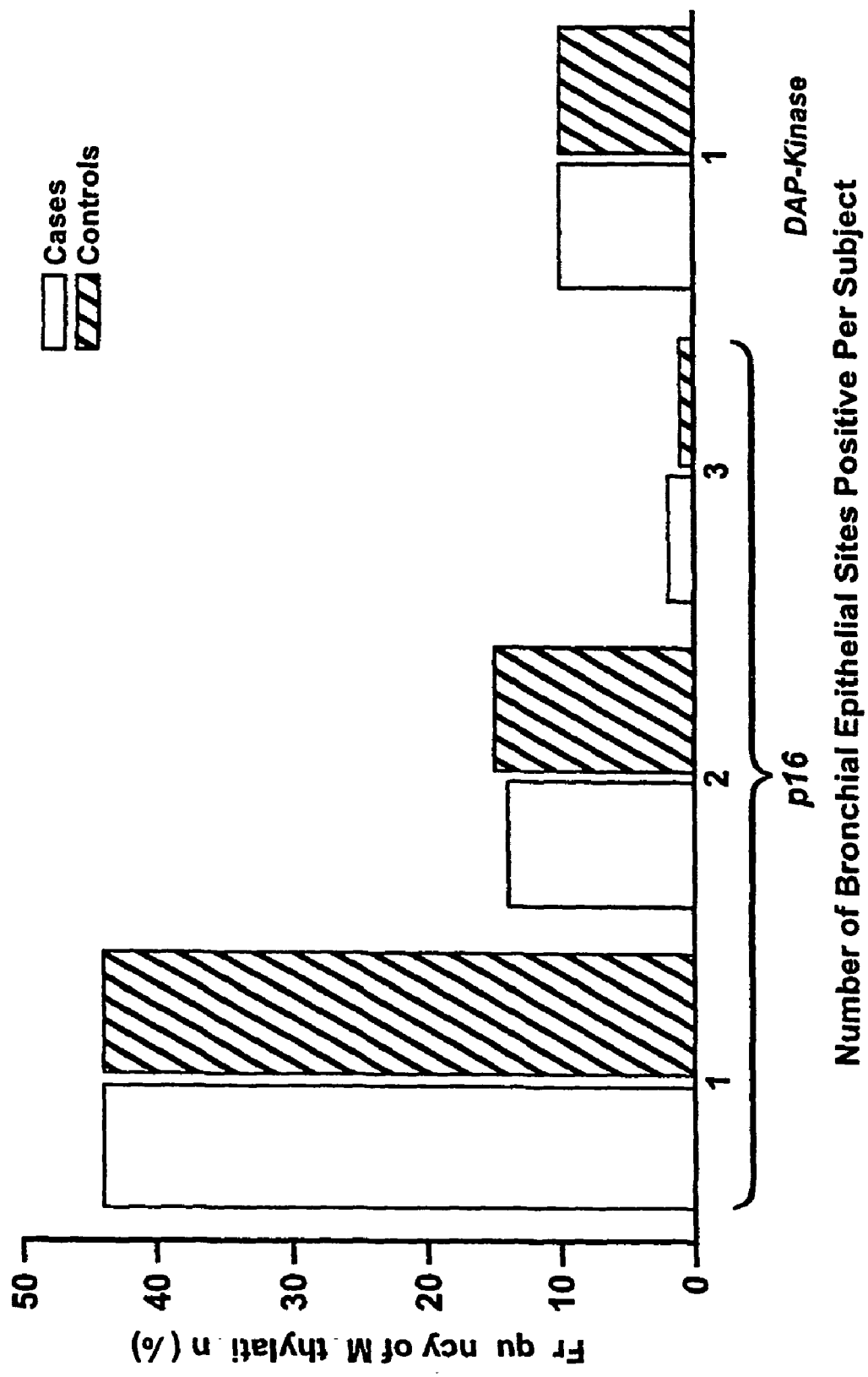
FIG. 10 is a graph showing the number of bronchial epithelial sites positive (by frequency of methylation) per subject involved in an exemplar test demonstrative of the invention.

FIG. 9 depicts methylation of the p16 gene in BECs and corresponding sputum. Representative scenarios for detection of methylation in BECs and sputum from five different controls are shown. The sample number corresponds to an individual and the fraction (e.g. 1.1, 1.2) of BECs collected from different lung lobes from that individual. For example, in the first control, only the second bronchial epithelial site was positive for p16 methylation. CaLu6 and H2009 are cell lines known to contain a methylated and unmethylated p16 gene, respectively. FIG. 10 illustrates aberrant promoter hypermethylation in nonmalignant BECs from lung cancer cases and controls. Summary data are presented as the frequency of methylation (percent of persons positive) at one to three bronchial epithelial sites for the p16 and DAP-kinase genes.

BEC cultures were successfully established from 94% of the collected sites allowing the methylation state of the p16 MGMT, DAP-kinase, and RASSF1A genes to be examined in 160 and 137 sites from cases and controls, respectively. Aberrant promoter methylation of the p16 gene was seen in at least one site from 44% of both cases and controls, and 14% and 15% of cases and controls, respectively, had two sites positive, as seen in FIGS. 9 and 10. Further, two cases and one control had three sites positive, but no subjects had methylation of p16 in all four BEC sites (FIG. 2). The prevalence for methylation of the DAP-kinase gene in bronchial epithelium was significantly less than observed for p16 irrespective of case-control status (p—0.001). Only five cases (10%) and four controls (10%) had a BEC site positive for methylation of the DAP-kinase gene; as indicated in FIG. 10, methylation was never seen in more than one site in a subject. Methylation of the RASSF1A gene was not detected in any sites. Interestingly, methylation of both p16 and DAP-kinase was seen in two cases and one control. Only in the control subject was the methylation found at the same site. Methylation of p16, DAP-kinase, or RASSF1A was not detected in any of the 17 sites from seven never-smokers (not shown), a finding consistent with previous studies that have reported virtually no genetic alterations in bronchial epithelium from this population).

In marked contrast to the findings for these three genes in BECs, methylation of the MGMT gene was observed in >75% of BEC sites from cases and controls. In addition, MGMT methylation was seen in 14 of 17 sites from the never-smokers (not shown). This finding has also been observed in normal human fibroblasts, which displayed extensive methylation of the MGMT CpG island as they became confluent. The process was partially reversed when fibroblasts were placed back into logarithmic growth. Thus, in the tissue culture setting, it is apparent that confluence-induced growth constraint must cause transient alterations in epigenetic stability within the MGMT promoter, leading to aberrant methylation. The fact that the applicants' BECs were grown to 80% confluence, coupled with the use of the inventive two-stage MSP approach, facilitated the detection of this in vitro methylation. MGMT nevertheless may be used as a biomarker in sputum, since the high prevalence for the changes seen in vitro occur in a context quite distinct from that of the airway epithelium. Furthermore, this determination is not recapitulated in either primary NSCLCs or exfoliated cells within sputum where the prevalence for MGMT methylation is 25% and 15%, respectively.

For the cases, there was no association between tumor histology and methylation of the p16 of DAP-kinase genes in the bronchial epithelium. This finding is consistent with the fact that these genes are methylated in both SCC and adenocarcinome. Smoking status had no association with the detection of methylation of either the p16 or DAP-kinase gene in the bronchial epithelium. Thus, promoter methylation was seen as frequently in BECs from current smokers as from former smokers. In addition, none of the smoking variables categorized (duration, pack years, time quit) was associated with the detection of promoter methylation in the bronchial epithelium.

A correlation was observed between p16 status in BECs and lung tumors. Tumor tissue was available from 18 of the cases diagnosed with lung cancer. To determine where p16 methylation in the BECs within these cases predicts methylation at this locus in tumors, DNA was isolated from microdissected tumors for MSP analysis of p16. Methylation of the p16 gene was detected in four of eight SCCs, four of eight adenocarcinomas, and one of two NSCLCs (not shown). Seventeen of the 18 tumors showed an absolute concordance (p<0.001), being either both methylated in the tumor and at least one BEC site (nine pairs) or unmethylated in the tumor and BECs (eight pairs). In the one discordant tumor-BEC pair, the bronchial epithelium was methylated, and the tumor was unmethylated.

The studies of Example One above for p16 and MGMT methylation in a limited number of cancer-free smokers suggest that the prevalence for these changes approximate lifetime risk for lung cancer. Thus, during the recruitment of subjects for this case-control study, the protocol was amended to include the collection of sputum from controls in order to gather additional information on the prevalence of the p16, MGMT, DAP-kinase, and RASSF1A genes in this population of veterans. Sputum was obtained from 66 controls; 18 underwent bronchoscopy.

Figure 11:
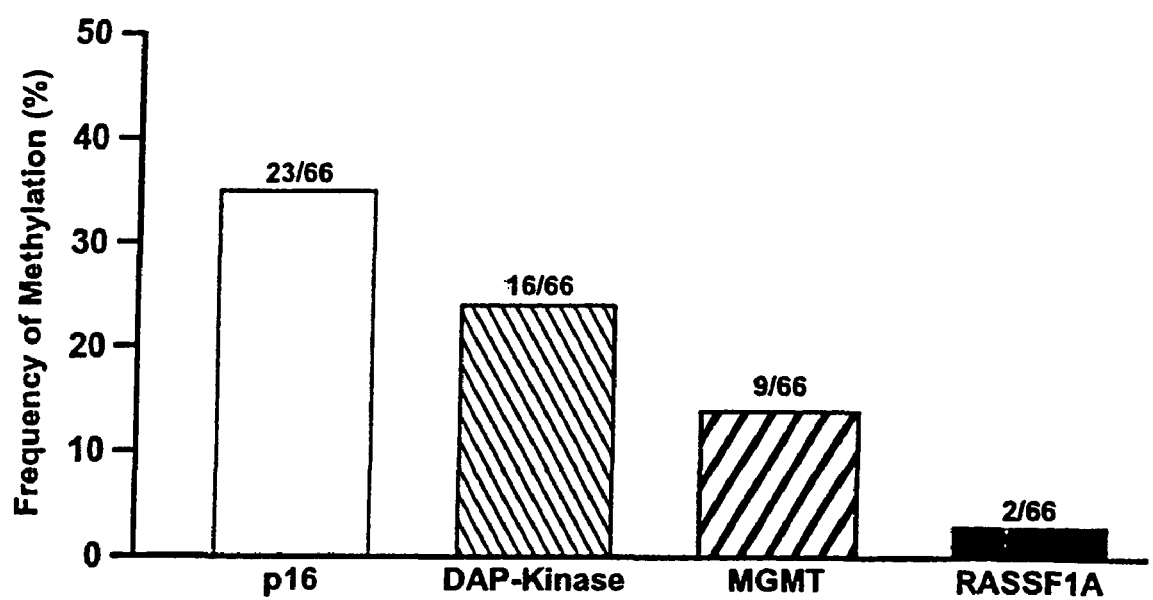
FIG. 11 is a graph showing relative frequency of methylation for p16 gene, DAP-Kinase gene, MGMT gene, and RASSF1A gene in exemplar tests demonstrative of the invention.
Figure 12:
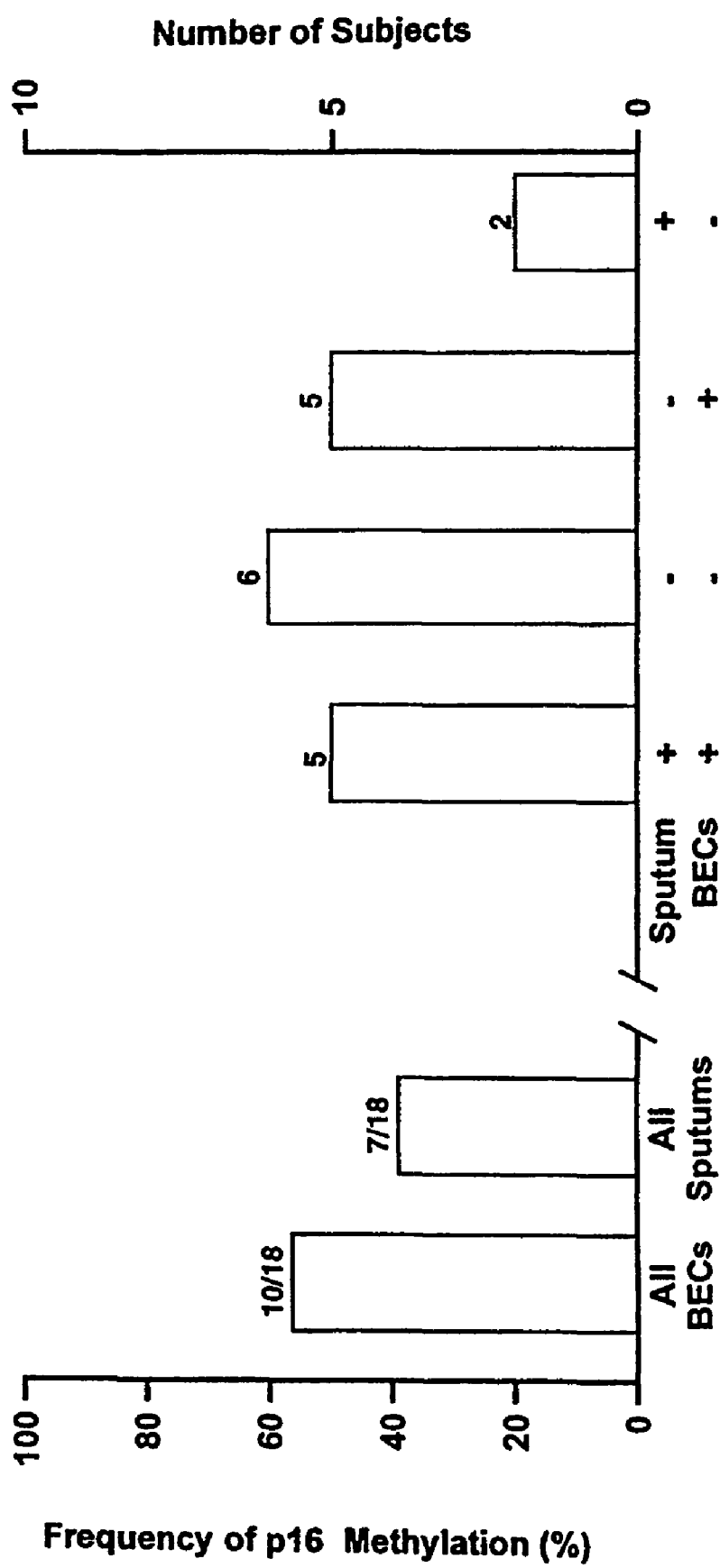
FIG. 12 is a graph comparing sputum samples by frequency of methylation, and number of subjects, in exemplar tests demonstrative of the invention.

FIG. 11 shows aberrant promoter hypermethylation in sputum from cancer-free controls. Summary data are presented as the frequency for methylation of the p16, MGMT, DAP-kinase, and RASSF1A genes in sputum collected from 66 cancer-free controls. The total number of positive samples per total sample population is depicted above the bar graphs in the figure. Reference also is made to FIG. 12, showing the relationship between p16 methylation in BECs and sputum. The overall frequency for methylation of p16 in BECs and matched sputum samples from 18 cancer-free controls is depicted on the left horizontal axis of the figure. The relationship between methylation in the BECs and sputum is displayed by four possible situations: (1) positive sputum, positive BEC; (2) negative sputum, negative BEC; (3) negative sputum, positive BEC; and (4) positive sputum, negative BEC. The number of subjects who fit into each category is indicated above the bar graph.

Abnormal sputum cytology was seen in 25% of controls. Metaplasia was the most common change, being present in 19% of sputum samples, while mild dysplasia was observed in 6% of sputum samples. Methylation of the p16 gene was detected in sputum from 23 of 66 controls (35%; FIG. 11). DAP-kinase methylation was also seen in sputum from 16 controls, and eight of these subjects were positive for methylation of p16, as seen in FIG. 11. MGMT methylation was seen in nine controls, four of these subjects were also positive for either p16 (one subject) or DAP-kinase (three subjects). In addition, three subjects positive for MGMT methylation also had methylation of both p16 and DAP-kinase in their sputum (not shown). Methylation of RASSF1A was only detected in two sputum samples; however, one person positive for this gene contained p16, DAP-kinase, and MGMT methylation in the sputum sample. The other person's sputum was positive for DAP-kinase and MGMT methylation. Thus, three (5%) and one (2%) of the control subjects were positive for three or four of the methylation markers, respectively, in their sputum. As seen in Example One above, sputum cytology was not associated with positivity for aberrant promoter methylation. Smoking status had no association with the detection of gene promoter methylation in sputum. In addition, none of the smoking variables (duration, pack years, time quit) was associated with whether methylation was detected in the sputum.

The concordance between finding p16 methylation in sputum and bronchial epithelium from the 18 controls was examined. Reference is made to FIG. 12. In this subset, p16 methylation was seen in BECs and sputum of 10 and seven controls, respectively. Of the seven subjects whose sputum was positive for this market, five displayed the methylation change in their bronchial epithelium. Continuing reference to FIG. 12 shows that there were five controls whose bronchial epithelium was positive and sputum negative for p16 methylation.

The results of the test indicate that aberrant promoter hypermethylation of the p16 gene and to a lesser extent, DAP-kinase, occurs frequently in the bronchial epithelium of lung cancer cases and cancer-free controls who smoked. These methylation changes persist after smoking cessation. The changes are detected within exfoliated cells, supporting their use as markers in assessing lung cancer risk reduction in response to cancer chemopreventative agents. Prevalence and tissue multiplicity for the five genetic and epigenetic markers examined in this Example did not differentiate cases from controls. This determination has been corroborated by investigators examining other genetic markers, and is likely due to the overwhelming damage to the bronchial epithelium through years of exposure to tobacco carcinogens. Furthermore, the lack of any association between these markers and smoking does or duration may be due to the fact that 92% of cases and 73% of controls had >30 pack-years of smoking.

The fact that promoter methylation was seen at similar prevalences in cases and controls irrespective of smoking status (current versus former) does not challenge the suggestion that these methylation changes confer increased risk for lung cancer. Approximately half of the lung cancers are diagnosed in former smokers. While cessation of smoking is associated with a decrease in lung cancer risk, the cumulative risk for lung cancer by age 75 for a person who quits smoking at age 50 is still 5 times greater than a never smoker. Furthermore, the strong association seen between p16 methylation in the bronchial epithelium and corresponding primary tumor reinforces the concept that inactivation of genes such as p16, while not transforming by themselves, are most likely permissive for the acquisition of additional genetic and epigenetic changes that ultimately lead to malignant cancer. Supporting this concept are the findings from Example One above, where methylation of both p16 and MGMT was seen in sputum from 43% of persons with confirmed SCC, but only in 3% to 6% of cancer-free controls. Therefore, the time to acquire the additional genetic and epigenetic changes that promote tumor progression is likely a critical determinant for lung cancer risk.

Inactivation of the p16 gene by promoter hypermethylation was seen more frequently in bronchial epithelium than DAP-kinase, while RASSF1A methylation was never detected. This determination may reflect the timing and role of these genes in the development of lung cancer. Applicants have determined that p16 methylation is detected at the earliest cytologic stages of SCC and adenocarcinoma. Inactivation of p16 has been proposed as an early step to immortalization by allowing cells to escape the immortality checkpoint "MO". The importance of p16 in the development of NSCLC is evident by the fact that it is inactivated by promoter methylation in 60% to 70% of SCCs and up to 48% of adenocarcinomas.

The fact that promoter methylation was not seen in bronchial epithelium, and that only two sputum samples were positive for RASSF1A methylation, suggest that inactivation of this gene is a later event in malignant transformation. This conclusion is supported by the determination that both control subjects with RASSF1A methylation in their sputum also had methylation of at least two other genes (p16, MGMT, and/or DAP-kinase). These determinations indicate the potential utility of multiple markers for the ultimate development of risk profiles.

The p16 and DAP-kinase genes are inactivated by promoter hypermethylation in nonmalignant bronchial epithelium of current and former smokers, which is also detected in exfoliated cells within sputum. Sputum samples contain cells from the large bronchi and cells to a lesser extent from the smaller airways that include the small bronchi, bronchioles, and alveoli. A positive sputum sample reflected methylation in the bronchial epithelium 70% of the time.

The foregoing disclosure indicates that bronchial epithelial cells that harbor p16 or DAP-kinase genes inactivated through promoter hypermethylation persist after cessation of smoking. The impact that silencing of these and other critical regulatory genes has on absolute risk for lung cancer will be better addressed through the analysis of exfoliated cells within a biological fluid such as sputum that represents a composite of the genetic damage throughout the aerodigestive tract. Thus, the presence of promoter methylation in sputum from cancer-free smokers signals a higher risk for lung cancer.

The preceding examples can be repeated with similar success by substituting the generically or specifically described reactants and/or operating conditions of this invention for those used in the preceding examples.

FIGS. 5 and 6 summarize in tabular form the PCR primers and annealing temperatures, in degrees centigrade to perform, respectively, the first- and second-stage PCR method of the invention for various specified genes, including H-Cadherin, retinoic acid receptor beta, and fragile histidine triad. It is seen therefore, that the inventive method finds applicability on other gene types besides p16, MGMT, DAP-kinase, and RASSF1A.

Figure 7:
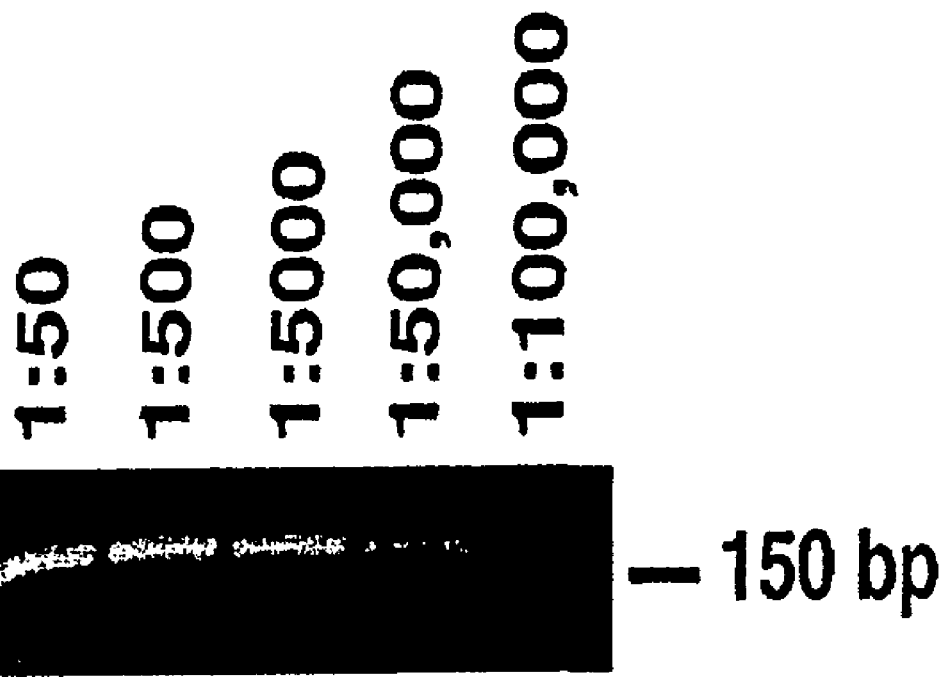
FIG. 7 is a graphical depiction of a CaLu6 cell line containing a methylated p16 gene, illustrating the dramatically increased sensitivity of the methylation specific polymerase chain reaction method of the invention for detecting p16 gene methylation. Depicted in Lanes 1–5 are the results of the stage-2 PCR with methylation-specific primers. The PCR product indicative of methylation is readily seen in DNA diluted up to 50,000 fold with normal DNA (lanes 1–5).

FIG. 7 illustrates the improved sensitivity for detection of p16 methylation according to the invention. The CaLu6 cell line contains a methylated p16 gene. DNA isolated from this cell line was serially diluted with DNA isolated from normal human lung. The DNA was then modified by bisulfite, and primers flanking the CaLu6 promoter region were used for stage-1 PCR. Depicted in Lanes 1–5 of the figure are the results of the stage-2 PCR with methylation-specific primers. The PCR product indicative of methylation is readily seen in DNA diluted up to 50,000 fold with normal DNA (lanes 1–5).

The invention offers a highly sensitive, robust, and reproducible test. Equally important, the invention contributes to cancer diagnosis and monitoring of all forms of cancer. The nested approach reduces the problem encountered in amplification of DNA targets (specific gene fragments) that are of suboptimal quality (partially degraded). The quality of DNA recovered from sputum and/or plasma is often partially degraded, meaning that the size of the DNA is less than what is found in healthy tissue. The impact of this on PCR is a reduction in the actual amount of specific DNA target that can be amplified and, ultimately, the sensitivity to detect the altered gene. Because the invention first expands the number of copies of the gene being evaluated, the amount of material used in the second PCR can be adjusted based on the quantity of product generated through the first PCR. In addition, because the annealing temperatures (the temperature by which the specific primers attach to the complementary target DNA) are raised in the second PCR, this greatly reduces the chance for getting a false positive result, a critical issue in the development of an accurate diagnostic test.

Further, while this disclosure has provided examples where a single gene (e.g. p16) has been the subject of the examination for a given polymerase chain reaction, it should be noted that the inventive method may be practiced where a plurality of two or more genes are examined for methylation in the course of a single procedure. For example, subject to limitations requiring significant differences in molecular weights, a single nested PCR procedure according to the invention may be practiced to look simultaneously for more than one marker, such as methylation of both p16 and MGMT. Risk profiles, for example, may be developed by looking at combinations of markers assayed with the invention. Accordingly, the inventive method may entail the concurrent assaying in a single reaction of multiple markers in biological fluids to determine risk, and perform monitoring, prevention, and prognosis. Further, different markers may be the subject of separate procedures to offer additive detection monitoring value, and increased efficiency and reliability of the overall evaluation.

The method of the invention may be practiced through the use of a laboratory kit. Kits for practicing the invention may be adapted to provide the materials needed to perform analysis specific to a particular type of body fluid, and/or customized to pertain to specific promotor genes of interest to the technician.

The development of methylation biomarkers using the invention allows the detection of many types of early cancers that would include but not be limited to lung, liver, head and neck, leukemia, colorectal, prostate, and bladder. Once the resulting tumor is identified and appropriate intervention is taken, the biomarkers can also be used to monitor disease reoccurrence and response to adjuvant therapy such as chemotherapeutics. An additional application of the technology relates specifically to lung cancer where often the tumor is not accessible for large-scale tissue sampling. Using biological fluids such as serum, plasma, or sputum, it is possible to determine non-invasively the genes inactivated by promoter hypermethylation. This information can be used to customize therapy.

Finally, many cancers take years to develop and susceptible persons go through a period of premalignancy where cells or DNA may be shed that harbor methylation biomarkers. The invention is useful for identifying individuals who subsequently could be enrolled in prevention intervention studies using dietary supplements that are designed to impede or reverse this premalignant state. The methylation biomarkers may also be used to monitor the efficacy of the interventions, by determining whether the previously detected methylation biomarker persists or disappears during the course of the intervention. The efficacy of any of the interventions known in the art, including but not limited to immunological modulation, gene therapy, antisense treatment, alkylating treatments, and the like, may be monitored.

Although the invention has been described in detail with particular reference to these preferred embodiments, other embodiments can achieve the same results. Variations and modifications of the present invention will be obvious to those skilled in the art. The entire disclosures of all references, patents, and publications cited above are hereby incorporated by reference.

What is claimed is:

1. A method of monitoring for cancer in cells, comprising detecting the presence of gene-specific promoter methylation of DNA from cells, comprising the steps of:
 a) subjecting the DNA to bisulfite modification;
 b) expanding the number of copies of at least one specific gene by using a polymerase chain reaction with a first primer set to amplify a portion of the gene where the promoter methylation resides, thereby generating an amplification product; and
 c) using an aliquot of the amplification product generated by the first polymerase chain reaction in a second, methylation-specific, polymerase chain reaction with a second primer set at a temperature of annealing that exceeds the melting temperature of the second primer set to amplify a portion of the gene's CpG island where the promoter methylation resides, and to detect the presence of inactivation of at least one specific gene.

2. The method of claim 1 wherein the step of expanding the number of copies of at least one specific gene comprises expanding the number of copies of more than one specific gene.

3. The method of claim 2 wherein the step of expanding the number of copies of more than one gene comprises expanding the number of copies of at least two genes in a single reaction selected from the group consisting of p16, MGMT, RASSF1A gene, H-Cadherin, retinoic acid receptor beta gene, and fragile histidine triad gene.

4. The method of claim 1 wherein the step of expanding the number of copies of a specific gene comprises amplifying a single gene.

5. The method of claim 4 wherein the step of expanding the number of copies of a single gene comprises amplifying the p16 gene.

6. The method of claim 5 wherein the step of amplifying the p16 gene comprises amplifying a 280 base pair fragment with a primer set comprising:
 Forward 5' GAGGGTGGGGCGGATCGC 3'
 Reverse 5' GACCCCGAACCGCGACCG 3'.

7. The method of claim 4 wherein the step of expanding the number of copies of a single gene comprises amplifying the MGMT gene.

8. The method of claim 7 wherein the step of amplifying the MGMT gene comprises amplifying a 289 base pair fragment with a primer set comprising:
 Forward 5' ACGTTTTGCGTTTCGACGTTC 3'
 Reverse 5' ACCCCCCACCCGACGACG 3'.

9. The method of claim 4 wherein the step of expanding the number of copies of a single gene comprises amplifying the DAP-kinase gene.

10. The method of claim 9 wherein the step of amplifying the DAP-kinase gene comprises amplifying the a 209 base pair fragment with a primer set comprising:
 Forward 5' ATAGTCGGATCGAGTTAACGTC 3'
 Reverse 5' AAAACTAACCGAAACGACGACG 3'.

11. The method of claim 4 wherein the step of expanding the number of copies of a single gene comprises amplifying the RASSF1A gene.

12. The method of claim 11 wherein the step of amplifying the RASSF1A gene comprises amplifying a 260 base pair fragment with a primer set comprising:
 Forward 5' GGGGGTTTTGCGAGAGCGC 3'
 Reverse 5' CCCGATTAAACCCGTACTTCG 3'.

13. The method of claim 1 in which said cells are human cells, and said at least one specific gene is the gene that is altered by the cancer.

14. The method of claim 13 wherein the human cells are from an obtained biological sample.

15. The method of claim 13 wherein the biological sample is selected from tissue plasma, ejaculate, cerebrospinal fluid, serum, mammary duct fluid, urine, and fecal stool and sputum.

16. The method of claim 14 wherein the step of expanding the number of copies of the gene comprises amplifying the p16 gene.

17. The method of claim 16 wherein the step of amplifying the p16 gene comprises amplifying a 280 base pair fragment with a primer set as indicated in claim 6.

18. The method of claim 14 wherein the step of expanding the number of copies of the gene comprises amplifying the MGMT gene.

19. The method of claim 18 wherein the step of expanding the number of copies of a specific gene comprises amplifying a 289 base pair fragment with a primer set as indicated in claim 8.

20. The method of claim 14 wherein the step of expanding the number of copies of a specific gene comprises amplifying the DAP-kinase gene.

21. The method of claim 20 wherein the step of expanding the number of copies of a specific gene comprises amplifying a 209 base pair fragment with a primer set as indicated in claim 10.

22. The method of claim 14 wherein the step of expanding the number of copies of a specific gene comprises amplifying the RASSF1A gene.

23. The method of claim 22 wherein the step of expanding the number of copies of a specific gene comprises amplifying a 260 base pair fragment with a primer set as indicated in claim 12.

24. A method according to claim 15 in which said method further comprises the step of contacting said DNA within said biological sample with a first primer set to expand the number of copies of a portion of the gene where the promoter CpG islands reside by using a polymerase chain reaction to generate an amplification product.

25. The method of claim 24 wherein the step of expanding the number of copies of the gene comprises amplifying the p16 gene.

26. The method of claim 25 wherein the step of amplifying the p16 gene comprises amplifying a 280 base pair fragment with a primer set as indicated in claim 6.

27. The method of claim 24 wherein the step of expanding the number of copies of the gene comprises amplifying the MGMT gene.

28. The method of claim 27 wherein the step of expanding the number of copies of a specific gene comprises amplifying a 289 base pair fragment with a primer set as indicated in claim 8.

29. The method of claim 24 wherein the step of expanding the number of copies of the gene comprises amplifying the H-Cadherin gene.

30. The method of claim 24 wherein the step of expanding the number of copies of the gene comprises amplifying the retinoic acid receptor beta gene.

31. The method of claim 24 wherein the step of expanding the number of copies of the gene comprises amplifying the fragile histidine triad gene.

32. The method according to claim 13 or 15, for detecting and monitoring a particular cancer in which said DNA is present either in the cell or free in the biological sample, and in which step b) comprises amplifying the portion of the gene's CpG island where the promoter methylation CpG islands resides by using a polymerase chain reaction thereby generating an amplification product containing fragments of a gene selected from the group consisting of the p16 gene, the MGMT gene, the DAP-kinase gene and the RASSF1A gene, to detect the presence of inactivation of the gene that is altered by the particular cancer.

33. The method of claim 32 further comprising the step of obtaining a sample of the biological fluid containing the gene that is altered by the cancer.

34. The method of claim 33 wherein the biological fluid sample obtained comprises sputum.

35. The method of claim 1 wherein the temperature of annealing is 4–6° C. above the melting temperature of the second primer.

* * * * *